(12) United States Patent
Baumgartner et al.

(10) Patent No.: US 9,193,935 B2
(45) Date of Patent: Nov. 24, 2015

(54) COMPOUNDS CAPABLE OF RELEASING FRAGRANT COMPOUNDS

(75) Inventors: Corinne Baumgartner, Fallanden (CH); Felix Flachsmann, Deubendorf (CH); Philip Kraft, Dübendorf (CH)

(73) Assignee: Givaudan S.A., Vernier (CH)

(*) Notice: Subject to any disclaimer, the term of this patent is extended or adjusted under 35 U.S.C. 154(b) by 136 days.

(21) Appl. No.: 13/996,158

(22) PCT Filed: Dec. 23, 2011

(86) PCT No.: PCT/EP2011/074003
§ 371 (c)(1),
(2), (4) Date: Jun. 20, 2013

(87) PCT Pub. No.: WO2012/085287
PCT Pub. Date: Jun. 28, 2012

(65) Prior Publication Data
US 2013/0316938 A1   Nov. 28, 2013

(30) Foreign Application Priority Data
Dec. 23, 2010 (GB) .................................. 1021864.2

(51) Int. Cl.
| | |
|---|---|
| *C11D 3/50* | (2006.01) |
| *C11B 9/00* | (2006.01) |
| *C07C 15/44* | (2006.01) |
| *C07C 15/50* | (2006.01) |
| *C07C 15/58* | (2006.01) |
| *C07C 43/215* | (2006.01) |
| *C07C 43/23* | (2006.01) |
| *C07C 45/34* | (2006.01) |
| *C07D 317/50* | (2006.01) |
| *C07D 317/54* | (2006.01) |

(52) U.S. Cl.
CPC ............... *C11B 9/0015* (2013.01); *C07C 15/44* (2013.01); *C07C 15/50* (2013.01); *C07C 15/58* (2013.01); *C07C 43/215* (2013.01); *C07C 43/23* (2013.01); *C07C 45/34* (2013.01); *C07D 317/50* (2013.01); *C07D 317/54* (2013.01); *C11B 9/0003* (2013.01); *C11B 9/0053* (2013.01); *C11B 9/0061* (2013.01); *C11B 9/0076* (2013.01); *C11D 3/507* (2013.01)

(58) Field of Classification Search
CPC ........... C11D 3/507; C11B 9/00; A61Q 13/00
USPC ...................................................... 510/101
See application file for complete search history.

(56) References Cited

U.S. PATENT DOCUMENTS

| | | |
|---|---|---|
| 3,115,530 A | 12/1963 | Cohen |
| 3,196,174 A | 7/1965 | Cohen |
| 2010/0216679 A1 | 8/2010 | Batchelor et al. |

FOREIGN PATENT DOCUMENTS

| | | |
|---|---|---|
| GB | 1014541 A | 12/1965 |
| GB | 1445231 A | 8/1976 |
| JP | 2001-072637 A | 3/2001 |
| JP | 2001-233707 A | 8/2001 |
| WO | WO 2009/030600 A1 | 3/2009 |

OTHER PUBLICATIONS

Hawkins, et al., "Autoxidation of Olefins", Journal of Applied Chemistry, Jan. 1956, pp. 1-11, vol. 6, London, England.
GB 1021864.2—Search Report, May 26, 2011.
PCT/EP2011/074003—International Search Report, Apr. 18, 2012.
PCT/EP2011/074003—International Written Opinion, Apr. 18, 2012.
PCT/EP2011/074003—International Search Report, Jun. 25, 2013.
Attygalle, et al., "Reaction gas chromatography without solvent for identification of nanogram quantities of natural products", Analytical Chemistry, vol. 55, No. 8, pp. 1379-1384, American Chemical Society, Atlanta, Georgia, U.S., 1983.
Babudri, et al., "A general approach to conjugated (E,E)—dienes through sequential coupling reactions", Tetrahedron Letters, vol. 35, No. 47, pp. 8847-8850, Elsevier, Great Britain, 1994.
Ganeshpure, et al., "Oxygenation of (E)-4-stilbenols catalysed by cobalt(II) schiff base chelates", Tetradhedron Letters, vol. 29, No. 50, pp. 6629-6632, Great Britain, 1988.
Petrov, et al., "Synthesis of undecyl- and dodecylbenzenes and their perhydrides", Russian Journal of General Chemistry, vol. 28, pp. 1761-6, Pleiades Publishing, Moscow, 1958. CAS Abstract No. 1959:6672.
Thoms, et al., "The perfume group. New high-molecular asymmetrical tertiary alcohols", Archiv der Pharmazie und Berichte der Deutschen Pharmazeutischen Gesellschaft, vol. 263, pp. 263-273, 1925. CAS Abstract No. 1925:19145.
Tsukamoto, et al., "Palladium(0) -catalyzed direct cross-coupling reaction of allyl alcohols with aryl- and vinyl-boronic acids", Chemical Communications, No. 10, pp. 1200-1201, RSC Publishing, Cambridge, Great Britain, Apr. 15, 2004.
Wang, et al., "Iridium as a general catalyst for the decarboxylative addition of aldehydes to alkynes", Journal of Organometallic Chemistry, vol. 696, No. 1, pp. 211-215, Elsevier, Amsterdam, Netherlands, 2010. CAS Abstract No. 2010:1533165.
Wright, et al., "Juvenilizing activity of compounds related to the juvenile hormone against pupae of the stable fly", Journal of Economic Entomology, vol. 65, No. 6, pp. 1644-167, Entomological Society of America, Washington D.C., 1972. CAS Abstract No. 1973:53007.

*Primary Examiner* — John Hardee
(74) *Attorney, Agent, or Firm* — Curatolo Sidoti Co., LPA; Joseph G. Curatolo; Salvatore A. Sidoti

(57) ABSTRACT

Provided is class of compounds of formula (I)

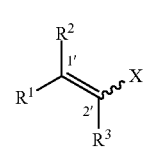

wherein X, $R^1$, $R^2$ and $R^3$ have the same meaning as given in the specification capable of releasing fragrant compounds in a controlled manner into the surroundings.

10 Claims, No Drawings

COMPOUNDS CAPABLE OF RELEASING FRAGRANT COMPOUNDS

CROSS REFERENCE TO RELATED APPLCATIONS

This application is a national stage application of International Application No. PCT/EP2011/074003, filed 23 Dec. 2011, which claims priority from Great Britain Patent Application No. 1021864.2, filed 23 Dec. 2010, from which application priority is claimed, and which are incorporated herein by reference.

The present invention relates to a particular class of compounds capable of releasing fragrant compounds in a controlled manner into the surroundings. The present invention is also concerned with a process for their production, and consumer products comprising them.

The provision of fragrance in products by addition thereto of inherently fragrant substances to products is well known and widely used. An alternative method of providing fragrance is by the use of a precursor, that is, a substance that is itself, basically because of the high molecular weight, essentially odorless, but which, in particular circumstances, will decompose to release the fragrant molecule.

There are several classes of compounds known which release fragrant molecules upon activation, such as hydrolysis, temperature change, oxygen, action of light and enzymes. According to our best knowledge only two classes of compounds have been reported to release upon oxidative cleavage odoriferous compounds. JP 2001-072637 discloses 2-alkoxy-3-arylpropenals (A) releasing functional substances. There are no details given with regard to the release mechanism nor with regard to any functional substance thus released. Yang et al. (*Helv. Chim. Acta* 2003, 86, 2928-2936) reports the release of aldehydes and ketones of p-amino alcohols (B) by periodate oxidation in $H_2O$ (=water).

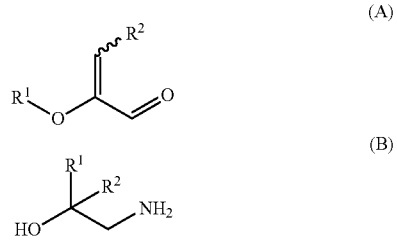

The systems reported in the prior art are often either too stable or too unstable and are therefore rather unsuitable as delivery systems for the controlled release of fragrances. It is therefore necessary to reach an optimal balance between stability and instability so as to obtain a release rate of the precursors as required for different applications, a task which is very difficult to achieve. In addition, the β-amino alcohols (B) described by Yang et al. release the aldehyde/ketone only in the presence of periodate, an additive which is not accepted in consumer products.

It has now been found that the compounds of formula (I) as hereinbelow described can act as precursors for the release, by spontaneous air oxidation, of an aldehyde or ketone and a further fragrant compound containing a carbonyl group.

Thus, there is provided in one aspect the use of a compound of formula (I)

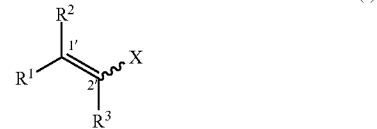

as precursor for generating a ketone or aldehyde of the formula (II)

and a carbonyl compound of the formula (III)

wherein $R^1$ is selected from the group consisting of $C_5$-$C_{14}$ alkyl, for example $C_6$-$C_{12}$ such as $C_8$, $C_9$, $C_{10}$ or $C_{11}$ alkyl;

$C_5$-$C_{14}$ alkenyl, for example $C_6$-$C_{12}$ such as $C_8$, $C_9$, $C_{10}$ or $C_{11}$ alkenyl comprising, e.g. one or two carbon-to-carbon double bonds;

$C_5$-$C_6$ cycloalkyl such as cyclohexyl, or cyclopentyl;

$C_5$-$C_8$ cycloalkyl (e.g. cyclohexyl, cyclopentyl) substituted with 1, 2, or 3 groups selected from $C_1$-$C_6$ alkyl (e.g. ethyl, isopropyl, tert-pentyl) and $C_2$-$C_4$ alkylidene (e.g. isopropenyl);

$C_5$-$C_8$ cycloalkenyl, e.g. $C_6$ cycloalkenyl such as cyclohexa-2,4-dienyl, cyclohex-1-enyl, cyclooct-3-enyl;

$C_5$-$C_8$ cycloalkenyl such as cyclooct-3-enyl, wherein the cycloalkenyl-ring is substituted with 1, 2, or 3 groups selected from $C_1$-$C_4$ alkyl (e.g. ethyl, or isopropyl), $C_2$-$C_4$ alkylidene (e.g. isopropenyl), and $C_3$-$C_5$ cycloalkyl (e.g. $R^1$ is 7-methyl-spiro[4.5]dec-8-en-6-yl, spiro[4.5]dec-7-en-7-yl, 5,5-dimethylcyclohex-1-enyl, 2,6,6-trimethylcyclohex-1,3-dienyl, 2,4-dimethylcyclohex-3-enyl, or 4-isopropenyl(cyclohex-1en-1yl);

($C_1$-$C_3$)alkyl($C_5$-$C_6$)cycloalkyl wherein the cycloalkyl-ring is optionally substituted with one group selected from —OH group and =O group, and/or one or two ether group(s), and/or up to four $C_1$-$C_5$ alkyl groups (e.g. $R^1$ is (3-tertbutyl-cyclohexyl)ethyl, or (4-(1,1-dimethylpropyl)cyclohexyl)methyl, (3-oxo-2-pentylcyclopentyl)methyl);

($C_1$-$C_4$)alkyl($C_5$-$C_6$)cycloalkenyl wherein the cycloalkenyl-ring is optionally substituted with one —OH group, and/or one or two ether group(s), and/or up to four (i.e. 0, 1, 2, 3 or 4) $C_1$-$C_5$ alkyl groups (e.g. (2,6,6-trimethylcyclohex-1-en-1-yl)ethyl, 1-(2,6,6-trimethylcyclohex-2-en-1-yl)butan-3-yl);

($C_2$-$C_3$)alkenyl($C_5$-$C_6$)cycloalkenyl wherein the cycloalkenyl-ring is optionally substituted with one —OH group, and/or one or two ether group(s), and/or up to four (i.e. 0, 1, 2, 3, or 4) $C_1$-$C_5$ alkyl groups (e.g. (2,6,6-trimethylcyclohex-1-en-1-yl)ethenyl, (2,6,6-trimethylcyclohex-2-en-1-yl)ethenyl, (2,6,6-trimethylcyclohex-2-en-1-yl)prop-2-en-2-yl, (2,6,6-trimethylcyclohex-1-en-1-yl)prop-2-en-2-yl);

$C_6$-$C_{14}$ aryl, e.g. phenyl;

$C_6$-$C_{14}$ aryl wherein the aryl ring is substituted with up to 3 (i.e. 0, 1, 2, or 3) groups selected from $C_1$-$C_4$ alkyl (e.g. ethyl, iso-propyl, tert-butyl), —O—CH$_2$—O—, and —OR$^{11}$ wherein R$^{11}$ is independently selected from hydrogen and $C_1$-$C_4$ alkyl (e.g. ethyl, iso-propyl, tert-butyl);

($C_1$-$C_3$)alkyl($C_6$-$C_{14}$)aryl, e.g. benzyl, 2-phenylethyl;

($C_1$-$C_3$)alkyl($C_6$-$C_{14}$)aryl such as benzyl or 2-phenylethyl wherein the aryl-ring is substituted with up to 2 groups (e.g. 1 group) selected from $C_1$-$C_4$ alkyl (e.g. ethyl, iso-propyl, tert-butyl), —O—CH$_2$—O—, and —OR$^{12}$ wherein R$^{12}$ is independently selected from hydrogen and $C_1$-$C_4$ alkyl (e.g. ethyl, iso-propyl, tert-butyl);

($C_2$-$C_8$)alkenyl($C_6$-$C_{14}$)aryl, e.g. 2-phenylethylene-1-yl, 1-phenylhept-1-en-2-yl;

($C_2$-$C_8$)alkenyl($C_6$-$C_{14}$)aryl wherein the aryl-ring is substituted with up to 2 groups (e.g. 1 group) selected from $C_1$-$C_4$ alkyl (e.g. ethyl, iso-propyl, tert-butyl), —O—CH$_2$—O—, and —OR$^{13}$ wherein R$^{13}$ is independently selected from hydrogen and $C_1$-$C_4$ alkyl (e.g. ethyl, iso-propyl, tert-butyl);

bi-, tri, or tetracyclic hydrocarbon ring comprising $C_8$-$C_{12}$ carbon atoms optionally substituted with up to 6 groups selected from $C_1$-$C_4$ alkyl (e.g. ethyl, iso-propyl, tert-butyl), —O—CH$_2$—O—, and —OR$^{14}$ wherein R$^{14}$ is independently selected from hydrogen and $C_1$-$C_4$ alkyl (e.g. ethyl, iso-propyl, tert-butyl), e.g. R$^1$ is 1,1,6,7-tetramethyl-1,2,3,4,5,6,7,8-octahydronaphthalen-7-yl, 2-((1,1-dimethyl-(2,3-dihydro-1H-indene))-6-yl)-eth-1-yl, 3,6,8,8-tetramethyl-2,3,4,7,8,8a-hexahydro-1H-3a,7-methanoazulen-5(4H)-ylidene, or 1,1,2,4,4,7-hexamethyl-1,2,3,4-tetrahydronaphthalene-6-yl;

R$^2$ is selected from hydrogen, $C_1$-$C_5$ alkyl, and $C_2$-$C_5$ alkenyl (e.g. but-3-enyl);

or

R$^1$ and R$^2$ form together with the carbon atom to which they are attached a) a 5 to 7 membered hydrocarbon ring(s), the ring(s) may contain up to two (i.e. 0, 1 or 2) ether groups, and/or the ring(s) may optionally be substituted with $C_1$-$C_5$ alkyl groups (e.g. methyl or 3-methylbutyl), for example, R$^1$ and R$^2$ forming together with the carbon atom to which they are attached is 7-methyl-3,4-dihydro-2H-benzo[b]([1,4]dioxepine-3-ylidene), 7-(1,1-dimethylethyl)-3,4-dihydro-2H-benzo[b]([1,4]dioxepine-3-ylidene), or 7-(3-methylbutyl)-3,4-dihydro-2H-benzo[b]([1,4]dioxepine-3-ylidene);

b) 2-(2-(4-methylcyclohex-3-en-1-yl)propyl)cyclopent-1-ylidene; or c) a 14-17 membered hydrocarbon ring (e.g. cyclohexadec-1-ene-6-ylidene, (Z)-cycloheptadec-1-ene-10-ylidene), the ring may be substituted with a methyl group (e.g. (Z)-4-methyl-cyclotetradec-1-ene-6-ylidene, 4-methyl-cyclopentadec-1-ene-6-ylidene;

R$^3$ is hydrogen or methyl; and

X means a radical of formula (Ia)

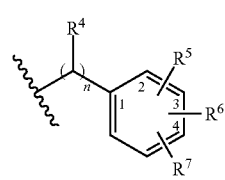

(Ia)

wherein n is 0 or 1;

R$^4$ is hydrogen or methyl;

R$^5$ is hydrogen or methyl;

R$^6$ is selected from hydrogen, $C_1$-$C_5$ alkyl, vinyl, hydroxyl, methoxy or ethoxy; and R$^7$ is selected from hydrogen, $C_1$-$C_5$ alkyl, vinyl, hydroxyl, methoxy or ethoxy; with the proviso that if one of R$^6$ and R$^7$ is hydroxyl then the other is selected from methoxy or ethoxy (e.g. if R$^7$=OH, then R$^6$=methoxy or ethoxy);

or

R$^6$ and R$^7$ form together with the carbon atoms to which they are attached a 5 or 6 membered ring containing up to two oxygen atoms (e.g. cyclopentane, cyclopentene, cyclohexane, cyclohexene, 1,3-dioxolane), wherein the ring may optionally be substituted with up to 6 methyl groups (e.g. 1, 2, or 5 methyl groups);

with the proviso that a) if n=0, R$^1$ is not a group selected from aryl and aryl substituted with an —OR$^{11}$ wherein R$^{11}$ is $C_1$-$C_4$ alkyl; and b) if R$^3$ is hydrogen and R$^1$ is selected from the group consisting of alkenyl, alkenylcycloalkenyl, alkenylaryl and cycloalkenyl in which no sp$^3$-hybridised C-atom is between C-1' and the nearest C—C double bond of R$^1$, then n=1.

Non-limiting examples are compounds of formula (I) wherein X is phenyl optionally substituted with up to 3 (i.e. 0, 1, 2 or 3) groups selected from $C_1$-$C_4$ alkyl (e.g. methyl, ethyl, iso-propyl, tert-butyl), vinyl, hydroxy, $C_1$-$C_3$ alkoxy (e.g. ethoxy), and —O—CH$_2$—O—, e.g. X is benzo[d][1,3]dioxol-5-yl, 3-methylphenyl, 4-methylphenyl, 4-methoxyphenyl, 4-vinylphenyl or 3-ethoxy-4-hydroxyphenyl.

Further, non-limiting examples are compounds of formula (I) wherein X is a radical of formula (Ia)

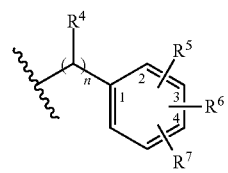

(Ia)

wherein R$^5$ is hydrogen or methyl and R$^6$ and R$^7$ form together with the C-3 and C-4 a 5 or 6 membered ring (e.g. cyclopentane, cyclopentene, cyclohexane, cyclohexene, 1,3-dioxolane) wherein the ring may optionally substituted with up to 5 methyl groups (e.g. 1 or 2 methyl groups).

Further, non-limiting examples are compounds of formula (I) wherein X is a radical of formula (Ib)

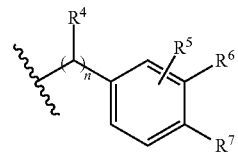

(Ib)

wherein n=0 or 1, R$^4$ and R$^5$ independently of each other are selected from hydrogen and methyl, and R$^6$ and R$^7$ independently of each other are selected from hydrogen, $C_1$-$C_5$ alkyl, vinyl, hydroxyl, methoxy or ethoxy.

Further, non-limiting examples are compounds of formula (I) wherein X is selected from naphthyl (e.g. naphth-2-yl), (naphthyl)methyl, 1,1,2,4,4,7-hexamethyl-1,2,3,4-tetrahydronaphthalen-6-yl, and 1,1,2,4,4,-pentamethyl-1,2,3,4-tetrahydronaphthalen-7-yl.

Further non-limiting examples are compounds of formula (I) wherein $R^1$ is $C_1$, $C_2$ or $C_3$ alkylphenyl wherein the phenyl ring is substituted with up to 3 (i.e. 0, 1, 2 or 3) groups selected from $C_1$-$C_4$ alkyl (e.g. iso-propyl, tert-butyl), hydroxy, $C_1$-$C_3$ alkoxy (e.g. ethoxy), and

Further, non-limiting examples are compounds of formula (I) wherein $R^2$ is hydrogen and $R^3$ is hydrogen or methyl.

Further, non-limiting examples are compounds of formula (I) wherein $R^2$ is hydrogen or methyl and $R^3$ is hydrogen.

Further, non-limiting examples are compounds of formula (I) wherein n=0, $R^2$ and $R^3$ are independently selected from hydrogen and methyl, $R^6$ is selected from hydrogen, methyl and hydroxyl, and $R^7$ is selected form hydrogen, methoxy and ethoxy, with the proviso that if $R^6$ is hydroxyl than $R^7$ is methoxy or ethoxy.

Further, non-limiting examples are compounds of formula (I) wherein $R^2$ is hydrogen or methyl, $R^3$ is hydrogen, and $R^1$ is ($C_1$-$C_3$)alkyl($C_6$-$C_{14}$)aryl wherein the aryl-ring is optionally substituted with one group selected from methoxy and hydroxyl.

Further, non-limiting examples are compounds of formula (I) wherein $R^1$ is $C_5$-$C_{14}$ alkenyl comprising one carbon-to-carbon double bond, $R^2$ is hydrogen, and $R^3$ is hydrogen, with the proviso that the carbon-to-carbon double bond is not in alpha position to C-1'.

Further, non-limiting examples are compounds of formula (I) wherein $R^1$ is $C_5$-$C_{14}$ alkenyl comprising one carbon-to-carbon double bond, $R^2$ is hydrogen, and $R^3$ is methyl.

As used in relation to compounds of formula (I) unless otherwise indicated "alkyl" refers to linear or branched alkyl wherein the alkyl residue may comprise up to one —OH group and up to 2 (i.e. 0, 1 or 2) ether group(s), such as undecan-2-yl, 2,4,4-trimethylpentyl, 2,6-dimethylheptyl, and 6-methylheptan-2-yloxypropyl; "alkenyl" refers to linear or branched alkyl comprising at least one carbon-to-carbon double bond, e.g. 2 or 3 double bonds, the alkenyl may optionally comprise a —OH group and/or ether group, for example oct-1,5-dienyl, non-3-enyl, and 2,6-dimethylhept-1,5-dienyl; "hydrocarbon ring" refers to saturated and unsaturated ring systems, preferably containing up to two carbon-to-carbon double bonds per ring, wherein the ring may be substituted with up to 3 (e.g. one or two) $C_1$-$C_3$ alkyl; and "ether group" refers to an oxygen atom connected to two carbon atoms.

With regard to the compounds of formula (I) the wavy bond means that the arrangement at the ethylenic double bond may be either in E- or Z-configuration.

All the compounds of formula (I) hereinabove described have in common the fact that, on exposure to ambient air they release volatile compounds over a long period of time (e.g. several days such as 2-7 days or even longer). In a preferred embodiment, at least one of the released compounds is a fragrant compound. In a further embodiment the compound of formula (II) is a fragrant aldehyde (for $R^2$=H) or ketone (for $R^2 \neq H$) and a second compound is a fragrant carbonyl compound of formula (III).

Examples of fragrant aldehydes O=CHR$^1$ which may be released from the compound of formula (I) under activating conditions include, but are not limited to, the following: benzaldehyde, 2,6,10-trimethylundec-9-enal, 8,8-dimethyl-1,2,3,4,5,6,7,8-octahydro-naphthalene-2-carbaldehyde, (4-isopropyl-phenyl)-ethanal, 2,4-dimethyl-cyclohex-3-ene-1-carbaldehyde, 1,3,5-trimethyl-cyclohex-1-ene-4-carbaldehyde, 4-(4-hydroxy-4-methylpentyl)-cyclohex-3-ene-1-carbaldehyde, hex-2-enal, hex-3-enal (including (Z)-hex-3-enal), 3-(3-tert-butylcyclohexyl)propanal, 2-(4-tert-pentylcyclohexyl)acetaldehyde, 3,5,5-trimethyl-hexanal, heptanal, 2,6-dimethyl-hept-5-enal, decanal, dec-9-enal, dec-4-en-1-al, 2-methyl-decanal, undec-10-en-1-al, undecanal, dodecanal, 2-methyl-undecanal, tridecanal, tridec-2-enal, octanal, nonanal, non-2-enal, undec-9-enal, 2-phenyl-propanal, 2-(4-methyl-phenyl)-ethanal, 2-(4-methoxyphenyl)acetaldehyde, 3,7-dimethyl-octanal, dihydrofarnesal (3,7,11-trimethyldodeca-6,10-dienal), 7-hydroxy-3,7-dimethyl-octanal, 2,6-dimethyl-oct-5-en-1-al, 3-(3-isopropyl-phenyl)-butanal (Florhydral), 4-(4-methyl-pent-3-enyl)-cyclohex-3-ene-1-carbaldehyde, 2,3,5,5,-tetramethyl-hexanal, decahydro-4,8,8-trimethyl-1,4-methanoazulene-9-carboxaldehyde (longifolic aldehyde), 2-methyl-3-(4-tert-butylphenyl)-propanal (Lilial), 3-(4-tert-butyl-phenyl)-propanal, 3-(4-isobutyl-phenyl)-propanal, 3-(benzo[1,3]dioxol-5-yl)-2-methyl-propanal, 3,7-dimethyl-oct-6-ene-1-al, 3,7-dimethyl-octanal, 2-methyl-3-(4-isopropylphenyl)-propanal, 4-tert-butyl-cyclohexane-1-carbaldehyde, 4-(octahydro-4,7-methano-5H-inden-5-ylidene)-butanal, (3,7-dimethyl-oct-6-enyloxy)-ethanal, 2 (E),6 (Z)-nonadienal, 2,4-dimethyl-2,6-heptadienal, (E)-dec-2-enal, dodec-2-enal, 3,7-dimethyl-octa-2,6-dienal, 2,4-diethyl-hepta-2,6-dienal, 3,7-dimethyl-nona-2,6-dienal, 2-propyl-hept-2-enal, 3-(4-methoxyphenyl)-2-methylpropanal, 4-methoxybenzaldehyde, 1,3-benzodioxole-5-carboxaldehyde, 2,6,6-trimethylcyclohexa-1,3-dienecarbaldehyde, 4-((6-methylheptan-2-yl)oxy)butanal, 3-(4-ethylphenyl)-2,2-dimethylpropanal, (E)-2-benzylideneheptanal, cinnamaldehyde, 3-(3,3-dimethyl-2,3-dihydro-1H-inden-5-yl)propanal, 2-methyl-4-(2,6,6-trimethylcyclohex-2-en-1-yl)butanal (Cetonal) and 4-isopropenyl-cyclohex-1-ene-1-carbaldehyde.

Examples of fragrant ketones O=CR$^1$R$^2$ which may be released from the compound of formula (I) under activating conditions include, but are not limited to, the following: Raspberry Ketone (4-(4-hydroxyphenyl)butan-2-one), Ionones such as alpha-Ionone, dihydro alpha-Ionone, dihydro beta-Ionone, N-allyl alpha-ionone (1-(2,6,6-trimethyl-2-cyclohexen-1-yl)-1,6-heptadien-3-one), beta-Ionone, N-methyl alpha-ionone (1-(2,6,6-trimethylcyclohex-2-en-1-yl)pent-1-en-3-one), dimethyl alpha-ionone (2-methyl-1-(2,6,6-trimethylcyclohex-2-en-1-yl)pent-1-en-3-one), and Cetone Alpha (3-methyl-4-(2,6,6-trimethylcyclohex-2-en-1-yl)but-3-en-2-one), Nectaryl (2-(2-(4-methylcyclohex-3-en-1-yl)propyl)cyclopentanone), Magnolione (3-(2-oxopropyl)-2-pentylcyclopentanone), Acetophenone, Oranger Crist (1-(naphthalen-2-yl)ethanone) and Cassione (4-(benzo[d][1,3]dioxol-5-yl)butan-2-one).

Examples of fragrant compounds of formula (III) O=CR$^3$X which may be released from the compound of formula (I) under activating conditions include, but are not limited to, the following: Ethylvanilin, Vanillin, Oranger Crist (1-(naphthalen-2-yl)ethanone), acetophenone, Heliotropine (1,3-benzodioxole-5-carboxaldehyde), anisic aldehyde, veratric aldehyde, phenylacetic aldehyde, Syringa Aldehyde (4-methyl phenylacetaldehyde), benzaldehyde, 3-methyl-benzaldehyde, 1-(4-methoxyphenyl)ethanone (Acetanisole), 4-(1-methylethyl)-benzenacetaldehyde, Ambral (2,4-(di-(1,1-dimethylethyl))-5-methoxy-benzaldehyde), 4-isopropyl-benzaldehyde, 1-(2,4-dimethylphenyl)ethanone, Fixal (5,5,7,8,8-pentamethyl-5,6,7,8-tetrahydronaphthalene-2-carbaldehyde), Fixolide (1-(3,5,5,6,8,8-hexamethyl-5,6,7,8-tetrahydronaphthalen-2-yl)ethanone), Florantone T (1-(5,6,7,8-tetrahydronaphthalen-2-yl)ethanone), 1-(1,1,2,3,3,6-hexamethyl-2,3-dihydro-1H-inden-5-yl)ethanone, 2-(4-isopropylphenyl)propanal, Vulcanolide (3,5,5,6,7,8,8-heptamethyl-5,6,7,8-tetrahydronaphthalene-2-carbaldehyde) and Safraleine (2,3,3-trimethyl-2,3-dihydro-1H-inden-1-one).

The activating conditions, which lead to the cleavage step, comprise the presence of molecular oxygen. The concentration of oxygen in the air is sufficient for cleaving the compound of formula (I) in such a way, that the cleavage products can be detected in the ambient air, e.g. by olfaction or GC-MS analysis of headspace samples.

The compounds of formula (I) are very stable when not exposed to the ambient air, i.e. when stored in a diluent conventionally used in conjunction with odorants, such as dipropyleneglycol (DPG), isopropylmyristate (IPM), triethylcitrate (TEC) and alcohol (e.g. ethanol), and known odorants. Very good storage stability has been proven also when incorporated in consumer products such as detergent, shampoo and fabric conditioner. Thus the compounds of formula (I) may find use in a broad range of consumer products in which a prolonged and defined release of fragrant compounds is desired.

The compounds of formula (I) can act as fragrance precursors in functional and fine perfumery i.e. in fine fragrances, industrial, institutional, home and personal care products. Industrial, institutional and home cleaning products to which the compound of formula (I) can be added include all kinds of detergents, window cleaners, hard surface cleaners, all-purpose cleaners and furniture polishes. Preferably, the products are liquids, e.g. fabric conditioner compositions. A substrate, such as a fabric, treated with a product comprising a compound of formula (I), will diffuse a fresh and/or clean odor under cleavage conditions for much longer than one treated with a conventional product. Fabrics or clothes washed with such a fabric softener will exhibit noticeable fragrance release even after one week.

The compounds of the formula (I) are also useful for application in all kinds of body care products. Especially interesting products are hair care products, for example shampoos, conditioners and hairsprays, and skin care products.

The abovementioned examples are of course only illustrative and non-limiting. Many other products to which the compounds of formula (I) may be added include soaps, bath and shower gels and deodorants.

The compounds of formula (I) can be used alone, as a mixture thereof, or in combination with other fragrance ingredients and/or precursors thereof. Such fragrance ingredients are described, for example, in "Perfume and Flavor Chemicals", S. Arctander, Ed., Vol. I & II, Allured Publishing Corporation, Carol Stream, USA, 2003 and include fragrance compounds of natural or synthetic origin and essential oils.

The amounts in which the compounds of formula (I) may be incorporated in the various above-mentioned products vary within a wide range. The amounts depend on the nature of the fragrant compounds to be released, the nature of the product to which the compounds of formula (I) are added and the desired olfactory effect. The amounts used also depend on the co-ingredients in a given composition when the compounds of formula (I) are used in admixture with perfuming co-ingredients, solvents or adjuvants. Typical concentrations are from 0.0001 to 5 weight percent of the article. In one embodiment, compounds of the present invention may be employed in a fabric softener in an amount of from 0.0001 to 0.2 weight percent. In another embodiment, compounds of the present invention may be used in fine perfumery in amounts from 0.001 to 10 weight percent (e.g. up to about 5 weight percent), more preferably between 0.02 and 4 weight percent. However, these values are given only by way of example, since the experienced perfumer may also achieve effects or may create novel accords with lower or higher concentrations.

While some of the compounds falling within the definition of the formula (I) above are known as intermediates, others are novel.

The invention therefore also provides a compound of formula (I) as hereinabove defined selected from (3-methyl-5-(2,6,6-trimethylcyclohex-1-enyl)pent-2-enyl)benzene; (5,9-dimethyldec-2-enyl)benzene; (4-methyltridec-2-enyl)benzene; (3-(2,4-dimethylcyclohex-3-enyl)allyl)benzene; (4-methyldodec-2-enyl)benzene; 1-isopropyl-3-(6-phenylhex-4-en-2-yl)benzene; but-2-ene-1,3-diyldibenzene; ((4E)-3-methyl-5-(2,6,6-trimethylcyclohex-1-enyl)penta-2,4-dienyl)benzene; (3-methyldodec-2-enyl)benzene; 5-(3-methyl-5-phenylpent-3-enyl)benzo[d][1,3]dioxole; ((4E)-3,4-dimethyl-5-(2,6,6-trimethylcyclohex-2-enyl)penta-2,4-dienyl)benzene; (4E,8Z)-undeca-2,4,8-trienylbenzene; (6E)-dodeca-2,6-dienylbenzene; 1-tert-butyl-4-(2-methyl-5-phenylpent-3-enyl)benzene; 1-(2,2-dimethyl-5-phenylpent-3-enyl)-4-ethylbenzene; (5,7,7-trimethyloct-2-enyl)benzene; (6-(6-methylheptan-2-yloxy)hex-2-enyl)benzene; (5-(3-tert-utylcyclohexyl)pent-2-enyl)benzene; (4-(4-tert-pentylcyclohexyl)but-2-enyl)benzene; 2-ethoxy-4-(3-phenylprop-1-enyl)phenol; 4-(3-methyl-5-phenylpent-3-enyl)phenol; 2-ethoxy-4-(3-p-tolylprop-1-enyl)phenol; 2-ethoxy-4-(3-(4-methoxyphenyl)prop-1-enyl)phenol; 1-methoxy-4-(4-methyltridec-2-enyl)benzene; 1-isopropyl-3-(6-(4-methoxyphenyl)hex-4-en-2-yl)benzene; 1-((6E)-dodeca-2,6-dienyl)-4-methoxybenzene; 2-(4-(4-methoxyphenyl)but-2-en-2-yl)naphthalene; 1-tert-butyl-4-(5-(4-methoxyphenyl)-2-methylpent-3-enyl)benzene; 1-methyl-4-(4-methyltridec-2-enyl)benzene; 1-((6E)-dodeca-2,6-dienyl)-4-methylbenzene; 1-tert-butyl-4-(2-methyl-5-p-tolylpent-3-enyl)benzene; 1-methyl-4-((4E)-3-methyl-5-(2,6,6-trimethylcyclohex-1-en-1-yl)penta-2,4-dien-1-yl)benzene; 5-(3-p-tolylprop-1-enyl)benzo[d][1,3]dioxole; 2-(4-methyltridec-2-enyl)naphthalene; 4-(3-methyl-4-phenylbut-3-enyl)phenol; 2-ethoxy-4-(4-(4-hydroxyphenyl)-2-methylbut-1-enyl)phenol; 2-ethoxy-4-(4-(3-isopropylphenyl)pent-1-enyl)phenol; 2-ethoxy-4-(3-methyldodec-1-enyl)phenol; 2-ethoxy-4-((2-(2-(4-methylcyclohex-3-enyl)propyl)cyclopentylidene)methyl)-phenol; 2-(5-(3-isopropylphenyl)hex-2-en-2-yl)naphthalene; 2-((4E,8Z)-undeca-2,4,8-trien-2-yl)naphthalene; 2-((6E)-dodeca-2,6-dien-2-yl)naphthalene; 2-(4-methyltridec-2-en-2-yl)naphthalene; 2-(5,7,7-trimethyloct-2-en-2-yl)naphthalene; 4-(4-(3-isopropylphenyl)pent-1-enyl)-1,2-dimethoxybenzene; 1,2-dimethoxy-4-(4-(4-methoxyphenyl)-3-methylbut-1-enyl)benzene; 5-(4-(3-isopropylphenyl)pent-1-enyl)benzo[d][1,3]dioxole; 5-(4-(4-methoxyphenyl)-3-methylbut-1-enyl)benzo[d][1,3]dioxole; 5-(4-(4-tert-butylphenyl)-3-methylbut-1-enyl)benzo[d][1,3]dioxole; 1-methoxy-4-(3-(p-tolyl)prop-1-en-1-yl)benzene; 1-(tert-butyl)-4-(4-(4-methoxyphenyl)-2-methylbut-3-en-1-yl)benzene; 4-(4-(4-methoxyphenyl)-3-methylbut-3-en-1-yl)phenol; 1-isopropyl-3-(5-(4-methoxyphenyl)pent-4-en-2-yl)benzene; 1-isobutyl-4-(4-(4-methoxyphenyl)but-3-en-1-yl)benzene; 2-((11E)-trideca-2,11-dien-2-yl)naphthalene; 5-(4-phenylbut-1-en-1-yl)benzo[d][1,3]dioxole; 1,2-dimethoxy-4-(3-(4-(prop-1-en-2-yl)cyclohex-1-en-1-yl)allyl)benzene; 2-(5-(4-(tert-butyl)phenyl)-4-methylpent-2-en-2-yl)naphthalene; 2-((4E)-5,9-dimethyldeca-2,4,8-trien-2-yl)naphthalene; 2-(5-phenylpent-2-en-2-yl)naphthalene; 2-((4E)-tetradeca-2,4-dien-2-yl)naphthalene; 3-(3-(4-methoxyphenyl)-2-methylallyl)-2-pentylcyclopentanone; 1-methoxy-4-

[(5E)-undeca-1,5-dien-1-yl]benzene; 1-methoxy-4-(3-methyldodec-1-en-1-yl)benzene; (1E)-1-[(4Z)-hepta-1,4-dien-1-yl]-4-methoxybenzene; (1Z)-1-[(4Z)-hepta-1,4-dien-1-yl]-4-methoxybenzene; and 4-[3-methyl-4-(m-tolyl)but-3-en-1-yl]phenol.

The compounds of formula (I) may be prepared starting from the respective fragrant carbonyl compound of formula (II) as hereinabove defined and a phosphorous ylide derived in situ from a 1- or 2-arylethyltriphenyl-phosphonium-halogen salt or an aryltriphenyl-phosphonium-halogen salt.

The phosphonium salts may be synthesized from the corresponding alkyl halides and triphenlyphosphine. The reaction can be carried out without solvent in a sealed tube or a round bottom flask at a temperature preferably between about 130-150° C. Alternatively, the reaction may be conducted in a round bottom flask in a solvent e.g. toluene, THF or MeCN and at a temperature between about 25-140° C. Benzylic phosphonium salts may also be synthesized from the corresponding benzylalcohols and triphenylphoshine hydrobromide. The reaction is conducted in a solvent e.g. toluene, THF or MeCN and at a temperature between about 25-140° C. The phosphorous ylides may be prepared from the crude phosphonium salts through deprotonation with a suitable base, e.g. R'Li, NaH, NaOR" or KOR", with R' being e.g. methyl, butyl or t-butyl and R" being e.g. methyl, ethyl, t-amyl or t-butyl. The reaction may be carried out in a solvent, e.g. THF or toluene. The base is added to the phosphonium salt at a temperature between about minus 78° C. to about 25° C.

The desired fragrant ketone/aldehyde of formula (II) may be added to the in situ prepared phosphorous ylide, preferably at a temperature between about minus 78° C. to about 25° C. and the reaction mixture may be stirred at a temperature between about 0-70° C.

Alternatively, the compounds of formula (I) may be prepared starting from the respective aldehyde/ketone of formula (III) as hereinabove defined and a phosphorous ylide derived in situ from a suitable triphenyl-phosphonium-halogen salt. The desired carbonyl compound of formula (III) may be added to the in situ prepared phosphorous ylide.

The invention is now further described with reference to the following non-limiting examples. These examples are for the purpose of illustration only and it is understood that variations and modifications can be made by one skilled in the art.

EXAMPLE 1

(3-Methyl-5-(2,6,6-trimethylcyclohex-1-enyl)pent-2-enyl)benzene

A solution of phenethyltriphenylphosphonium bromide (4.40 g, 9.84 mmol, 1.0 equiv.) in THF (20 mL) was cooled to 0° C. After adding n-BuLi (1.6 M in hexanes, 6.2 mL, 9.84 mmol, 1.0 equiv.) at 0° C., the red solution was stirred at 60° C. for 1 h. The mixture was re-cooled to 0° C., 4-(2,6,6-trimethylcyclohex-1-enyl)butan-2-one (1.92 g, 9.84 mmol, 1.0 equiv.) in THF (10 mL) was added, and the mixture was stirred at 70° C. for 20 h. After addition of $H_2O$, the aqueous layer was extracted with cyclohexane (2×), the combined organic phases were washed with brine, dried (MgSO4), filtered and the filtrate was concentrated. The residue was purified by flash chromatography on SiO2 (cyclohexane) to yield 816 mg (29%) of the title compound as a colorless oil.

$^1$H-NMR (CDCl$_3$, 400 MHz): 7.32-7.27 (m, 2H), 7.22-7.17 (m, 3H), 5.41-5.37 (m, 0.5H), 5.33-5.30 (m, 0.5H), 3.39 (t, J=7.8 Hz, 2H), 2.22-2.16 (m, 1H), 2.13-2.08 (m, 3H), 1.93 (q, J=6.4 Hz, 2H), 1.82-1.81 (m, 1.5H), 1.78-1.77 (m, 1.5H), 1.67 (s, 1.5H), 1.62 (s, 1.5H), 1.61-1.55 (m, 2H), 1.46-1.41 (m, 2H), 1.04 (s, 3H), 1.01 (s, 3H).

MS (EI): 282 (M$^+$, 6), 267 (1), 191 (12), 144 (11), 137 (100), 95 (67), 91 (33), 81 (42), 67 (10), 55 (9), 41 (18).

EXAMPLE 2.1-2.22

Following the general procedure as described in Examples 1 the following compounds have been prepared:

2.1 (5,9-Dimethyldec-2-enyl)benzene

Starting from phenethyltriphenylphosphonium bromide (3.85 g, 8.61 mmol, 1.0 equiv.), n-BuLi (1.6 M in hexanes, 5.4 mL, 8.61 mmol, 1.0 equiv.) and 3,7-dimethyloctanal (2.02 g, 12.9 mmol, 1.5 equiv.), 1.16 g (55%) of the title compound as a colorless oil was obtained after purification by flash chromatography on SiO$_2$ (cyclohexane).

$^1$H-NMR (CDCl$_3$, 400 MHz): 7.31-7.28 (m, 2H), 7.21-7.18 (m, 3H), 5.65-5.50 (m, 2H), 3.42 (d, J=7.1 Hz, 1.7H), 3.36 (d, J=6.3 Hz, 0.3H), 2.20-1.84 (m, 2H), 1.59-1.49 (m, 2H), 1.37-1.26 (m, 3H), 1.19-1.16 (m, 3H), 0.95-0.85 (m, 9H).

MS (EI): 244 (M$^+$, 17), 216 (1), 188 (1), 174 (5), 132 (8), 117 (41), 104 (100), 91 (67), 71 (47), 57 (67), 43 (46).

2.2 (4-Methyltridec-2-enyl)benzene

Starting from phenethyltriphenylphosphonium bromide (3.60 g, 8.05 mmol, 1.0 equiv.), n-BuLi (1.6 M in hexanes, 5.0 mL, 8.05 mmol, 1.0 equiv.) and 2-methylundecanal (2.25 g, 12.1 mmol, 1.5 equiv.), 1.33 g (61%) of the title compound as a colorless oil was obtained after purification by flash chromatography on SiO$_2$ (hexanes).

Odor description (dry-down of a 10% DPG solution after 24 hours on a smelling strip): honey, cistus, olibanum, floral.

$^1$H-NMR (CDCl$_3$, 400 MHz): 7.32-7.27 (m, 2H), 7.22-7.17 (m, 3H), 5.53-5.46 (m, 1H), 5.31-5.25 (m, 1H), 3.47-3.34 (m, 2H), 2.62-2.52 (m, 1H), 1.35-1.25 (m, 16H), 1.00 (d, J=6.8 Hz, 3H), 0.90 (t, J=6.8 Hz, 3H).

MS (EI): 272 (M$^+$, 7), 180 (3), 160 (4), 145 (33), 129 (13), 117 (50), 104 (100), 97 (24), 91 (52), 83 (23), 69 (27), 55 (26), 41 (23).

2.3 (3-(2,4-Dimethylcyclohex-3-enyl)allyl)benzene

Starting from phenethyltriphenylphosphonium bromide (3.67 g, 8.20 mmol, 1.0 equiv.), n-Buli (1.6 M in hexanes, 5.1 mL, 8.20 mmol, 1.0 equiv.) and 2,4-dimethylcyclohex-3-enecarbaldehyde (1.70 g, 12.3 mmol, 1.5 equiv.), 1.14 g (61%) of the title compound as a colorless oil was obtained after purification by flash chromatography on SiO$_2$ (cyclohexane).

1H-NMR (CDCl$_3$, 400 MHz): 7.32-7.28 (m, 2H), 7.22-7.18 (m, 3H), 5.63-5.22 (m, 3H), 3.50-3.36 (m, 2H), 2.33-2.29 (m, 0.2H), 2.23-2.15 (m, 0.8H), 2.10-2.01 (m, 1H), 1.96-1.90 (m, 2H), 1.73-1.65 (m, 4H), 1.54-1.43 (m, 1H), 0.97 (d, J=7.1 Hz, 2.6H), 0.92 (d, J=7.3 Hz, 0.4H).

MS (EI): 226 (M$^+$, 20), 211 (2), 198 (9), 144 (27), 129 (100), 115 (23), 107 (17), 91 (47), 82 (93), 67 (49), 53 (8), 41 (14).

2.4: ((4E)-5,9-Dimethyldeca-2,4,8-trienyl)benzene

Starting from phenethyltriphenylphosphonium bromide (3.48 g, 7.78 mmol, 1.0 equiv.), n-BuLi (1.6 M in hexanes, 4.9 mL, 7.78 mmol, 1.0 equiv.) and (E)-3,7-dimethylocta-2,6-dienal (1.78 g, 11.7 mmol, 1.5 equiv.), 0.54 g (29%) of the title compound as a light yellow oil was obtained after purification by flash chromatography on SiO$_2$ (cyclohexane).

$^1$H-NMR (CDCl$_3$, 400 MHz): 7.32-7.28 (m, 2H), 7.24-7.19 (m, 3H), 6.68-6.64 (m, 0.1H), 6.39-6.31 (m, 0.9H), 6.26-6.23 (m, 0.7H), 5.92-5.85 (m, 0.3H), 5.76-5.48 (m, 1H), 5.18-5.11 (m, 1H), 3.56 (d, J=6.3 Hz, 1.3H), 3.47-3.43 (m, 0.7H), 2.22-2.11 (m, 4H), 1.87-1.76 (m, 3H), 1.73-1.71 (m, 3H), 1.66-1.63 (m, 3H).

MS (EI): 240 (M$^+$, 5), 225 (1), 197 (2), 171 (10), 129 (18), 115 (11), 105 (4), 91 (100), 77 (5), 69 (13), 41 (14).

2.5 (5,9-Dimethyldeca-2,8-dienyl)benzene

Starting from phenethyltriphenylphosphonium bromide (3.48 g, 7.78 mmol, 1.0 equiv.), n-BuLi (1.6 M in hexanes, 4.9 mL, 7.78 mmol, 1.0 equiv.) and 3,7-dimethyloct-6-enal (1.80 g, 11.7 mmol, 1.5 equiv.), 0.97 g (51%) of the title compound as a colorless oil was obtained after purification by flash chromatography on SiO$_2$ (cyclohexane).

$^1$H-NMR (CDCl$_3$, 400 MHz): 7.32-7.29 (m, 2H), 7.22-7.18 (m, 3H), 5.67-5.52 (m, 2H), 5.16-5.12 (m, 1H), 3.43 (d, J=7.1 Hz, 1.7H), 3.37 (d, J=6.3 Hz, 0.3H), 2.22-1.98 (m, 4H), 1.71 (d, J=1.0 Hz, 3H), 1.64-1.62 (m, 3H), 1.61-1.51 (m, 1H), 1.47-1.38 (m, 1H), 1.26-1.16 (m, 1H), 0.95 (d, J=6.6 Hz, 2.5H), 0.91 (d, J=6.8 Hz, 0.5H).

MS (EI): 242 (M$^+$, 8), 227 (1), 199 (4), 157 (31), 138 (45), 129 (47), 117 (30), 109 (61), 91 (91), 81 (38), 69 (100), 55 (38), 41 (63).

2.6: 1-Isopropyl-3-(6-phenylhex-4-en-2-yl)benzene

Starting from phenethyltriphenylphosphonium bromide (5.00 g, 11.2 mmol, 1.0 equiv.), n-BuLi (1.6 M in hexanes, 7.0 mL, 11.2 mmol, 1.0 equiv.) and 3-(3-isopropylphenyl)butanal (3.20 g, 16.8 mmol, 1.5 equiv.), 2.54 g (82%) of the title compound as a colorless oil was obtained after purification by flash chromatography on SiO$_2$ (cyclohexane/EtOAc 997:3).

Odor description (dry-down of a 10% DPG solution after 24 hours on a smelling strip): floral, green, watery, syringe.

$^1$H-NMR (CDCl$_3$, 400 MHz): 7.33-7.14 (m, 5H), 7.09-7.05 (m, 4H), 5.58-5.44 (m, 2H), 3.32 (d, J=6.8 Hz, 1.6H), 3.28 (d, J=6.6 Hz, 0.4H), 2.91-2.85 (m, 1H), 2.82-2.75 (m, 1H), 2.47-2.38 (m, 2H), 1.29 (d, J=7.1 Hz, 3H), 1.25-1.23 (m, 6H).

MS (EI): 278 (M$^+$, 7), 263 (1), 187 (2), 147 (100), 131 (8), 115 (7), 105 (19), 91 (22), 77 (5), 43 (13).

2.7: But-2-ene-1,3-diyldibenzene

Starting from phenethyltriphenylphosphonium bromide (3.48 g, 7.78 mmol, 1.0 equiv.), n-BuLi (1.6 M in hexanes, 4.9 mL, 7.78 mmol, 1.0 equiv.) and acetophenone (1.40 g, 11.7 mmol, 1.5 equiv.), 0.75 g (46%) of the title compound as a colorless oil was obtained after purification by flash chromatography on SiO$_2$ (cyclohexane).

$^1$H-NMR (CDCl$_3$, 400 MHz): 7.42-7.13 (m, 10H), 5.97 (tq, J=7.4, 1.4 Hz, 0.25H), 5.65 (tq, J=7.6, 1.5 Hz, 0.75H), 3.57 (d, J=7.3 Hz, 0.5H), 3.32 (d, J=7.6 Hz, 1.5H), 2.14-2.14 (m, 0.75H), 2.08-2.07 (q, J=1.3 Hz, 2.25H).

MS (EI): 208 (M$^+$, 67), 193 (56), 178 (28), 165 (11), 130 (24), 115 (100), 103 (10), 91 (42), 77 (17), 65 (12), 51 (12), 39 (5).

2.8: (3,7-Dimethylocta-2,6-dienyl)benzene

Starting from phenethyltriphenylphosphonium bromide (3.48 g, 7.78 mmol, 1.0 equiv.), n-BuLi (1.6 M in hexanes, 4.9 mL, 7.78 mmol, 1.0 equiv.) and 6-methylhept-5-en-2-one (1.48 g, 11.7 mmol, 1.5 equiv.), 0.29 g (17%) of the title compound as a colorless oil was obtained after purification by flash chromatography on SiO$_2$ (cyclohexane).

$^1$H-NMR (CDCl$_3$, 400 MHz): 7.31-7.27 (m, 2H), 7.21-7.17 (m, 3H), 5.39-5.34 (m, 1H), 5.19-5.11 (m, 1H), 3.38 (d, J=7.3 Hz, 2H), 2.20-2.06 (m, 4H), 1.77-1.76 (m, 1.7H), 1.73 (br. s, 1.3H), 1.71 (s, 3H), 1.64 (s, 1.7H), 1.62 (s, 1.3H).

MS (EI): 214 (M$^+$, 11), 171 (17), 157 (9), 143 (37), 129 (57), 123 (23), 117 (29), 109 (6), 103 (14), 91 (57), 77 (13), 69 (100), 53 (11), 41 (71).

2.9: ((4E)-3-Methyl-5-(2,6,6-trimethylcyclohex-1-enyl)penta-2,4-dienyl)benzene Starting from phenethyltriphenylphosphonium bromide (4.44 g, 9.93 mmol, 1.0 equiv.), n-BuLi (1.6 M in hexanes, 6.3 mL, 10.1 mmol, 1.0 equiv.) and (E)-4-(2,6,6-trimethylcyclohex-1-enyl)but-3-en-2-one (2.86 g, 14.9 mmol, 1.5 equiv.), 1.69 g (61%) of the title compound as a light yellow oil was obtained after purification by flash chromatography on SiO$_2$ (cyclohexane/EtOAc 98:2).

$^1$H-NMR (CDCl$_3$, 400 MHz): 7.32-7.27 (m, 2H), 7.22-7.17 (m, 3H), 6.55 (d, J=16.2 Hz, 1H), 6.19 (d, J=16.2 Hz, 1H), 5.63-5.59 (m, 0.45H), 5.53-5.49 (m, 0.55H), 3.53 (d, J=7.6 Hz, 2H), 2.04-1.99 (m, 2H), 1.93-1.92 (m, 1.65H), 1.91-1.91 (m, 1.35H), 1.73 (d, J=1.0 Hz, 1.65H), 1.70 (s, 1.35H), 1.66-1.59 (m, 2H), 1.50-1.44 (m, 2H), 1.05 (s, 3H), 1.03 (s, 3H).

MS (EI): 280 (M$^+$, 12), 265 (2), 237 (1), 189 (6), 133 (15), 119 (100), 105 (17), 91 (53), 77 (10), 65 (6), 55 (13), 41 (13).

2.10: 5-(3-Methyl-5-phenylpent-3-enyl)benzo[d][1,3]dioxole

Starting from phenethyltriphenylphosphonium bromide (1.82 g, 4.07 mmol, 1.0 equiv.), n-BuLi (1.6 M in hexanes, 2.6 mL, 4.07 mmol, 1.0 equiv.) and 4-(benzo[d][1,3]dioxol-5-yl)butan-2-one (1.17 g, 6.10 mmol, 1.5 equiv.), 0.35 g (30%) of the title compound as a colorless oil was obtained after purification by flash chromatography on SiO$_2$ (cyclohexane/EtOAc 99:1).

$^1$H-NMR (CDCl$_3$, 400 MHz): 7.29-7.25 (m, 2H), 7.20-7.16 (m, 1H), 7.12-7.10 (m, 2H), 6.75-6.61 (m, 3H), 5.92 (s, 2H), 5.38-5.32 (m, 1H), 3.35 (d, J=7.3 Hz, 1H), 3.26 (d, J=7.3 Hz, 1H), 2.70-2.63 (m, 2H), 2.42-2.38 (m, 1H), 2.33-2.29 (m, 1H), 1.79-1.78 (m, 1.5H), 1.76-1.75 (m, 1.5H).

MS (EI): 280 (M$^+$, 14), 135 (100), 128 (3), 115 (3), 105 (5), 91 (8), 77 (15), 65 (4), 51 (8).

2.11: ((4E)-3,4-Dimethyl-5-(2,6,6-trimethylcyclohex-2-enyl)penta-2,4-dienyl)benzene Starting from phenethyltriphenylphosphonium bromide (2.80 g, 6.26 mmol, 1.0 equiv.), n-BuLi (1.6 M in hexanes, 3.9 mL, 6.26 mmol, 1.0 equiv.) and (E)-3-methyl-4-(2,6,6-trimethylcyclohex-2-enyl)but-3-en-2-one (1.94 g, 9.39 mmol, 1.5 equiv.), 0.36 g (20%) of the title compound as a colorless oil was obtained after purification by flash chromatography on SiO$_2$ (cyclohexane/EtOAc 995:5).

$^1$H-NMR (CDCl$_3$, 400 MHz): 7.30-7.27 (m, 2H), 7.22-7.15 (m, 3H), 5.38-5.35 (m, 1H), 5.30-5.26 (m, 1H), 5.04-5.00 (m, 1H), 3.37 (d, J=7.3 Hz, 2H), 2.50 (d, J=10.9 Hz, 1H), 2.03-1.99 (m, 2H), 1.82-1.81 (m, 6H), 1.63-1.59 (m, 3H), 1.48-1.39 (m, 1H), 1.22-1.16 (m, 1H), 0.93 (s, 3H), 0.83 (s, 3H).

MS (EI): 294 (M+, 2), 238 (11), 223 (3), 171 (12), 147 (100), 119 (9), 105 (10), 91 (27), 77 (6), 65 (4), 55 (6), 41 (9).

2.12 (4E,8Z)-Undeca-2.4.8-trienylbenzene

Starting from phenethyltriphenylphosphonium bromide (3.05 g, 6.82 mmol, 1.0 equiv.), n-BuLi (1.6 M in hexanes, 4.3 mL, 6.82 mmol, 1.0 equiv.) and (2E,6Z)-nona-2,6-dienal (1.41 g, 10.2 mmol, 1.5 equiv.), 0.94 g (61%) of the title compound as a colorless oil was obtained after purification by flash chromatography on $SiO_2$ (cyclohexane/EtOAc 995:5).

Odor description (dry-down of a 10% DPG solution after 24 hours on a smelling strip): green, fatty, watery, dark tea, nonadienal, floral, mimosa, cassie, violet.

$^1$H-NMR (CDCl$_3$, 400 MHz): 7.32-7.27 (m, 2H), 7.21-7.18 (m, 3H), 6.49-6.42 (m, 1H), 6.12-6.04 (m, 1H), 5.80-5.73 (m, 1H), 5.52-5.32 (m, 3H), 3.53 (d, J=7.6 Hz, 1.5H), 3.41 (d, J=6.8 Hz, 0.5H), 2.23-1.99 (m, 6H), 0.97 (t, J=7.6 Hz, 2.25H), 0.96 (t, J=7.3 Hz, 0.75H).

MS (EI): 226 (M+, 2), 211 (1), 197 (3), 157 (8), 129 (15), 115 (17), 91 (100), 79 (8), 65 (5), 41 (11).

2.13: (6E)-Dodeca-2,6-dienylbenzene

Starting from phenethyltriphenylphosphonium bromide (3.20 g, 7.15 mmol, 1.0 equiv.), n-BuLi (1.6 M in hexanes, 4.5 mL, 7.15 mmol, 1.0 equiv.) and (E)-dec-4-enal (1.66 g, 10.7 mmol, 1.5 equiv.), 1.08 g (62%) of the title compound as a colorless oil was obtained after purification by flash chromatography on $SiO_2$ (cyclohexane/EtOAc 997:3).

Odor description (dry-down of a 10% DPG solution after 24 hours on a smelling strip): aldehydic, green, honey, floral, citrus.

$^1$H-NMR (CDCl$_3$, 400 MHz): 7.31-7.27 (m, 2H), 7.21-7.17 (m, 3H), 5.61-5.51 (m, 2H), 5.46-5.39 (m, 2H), 3.41 (d, J=6.6 Hz, 1.7H), 3.34 (d, J=6.1 Hz, 0.3H), 2.26-1.95 (m, 6H), 1.39-1.23 (m, 6H), 0.90 (t, J=7.0 Hz, 3H).

MS (EI): 242 (M+, 2), 171 (5), 158 (17), 138 (35), 130 (100), 115 (31), 104 (25), 91 (96), 82 (26), 69 (74), 55 (53), 41 (44).

2.14: 2-(4-Phenylbut-2-en-2-yl)naphthalene

Starting from phenethyltriphenylphosphonium bromide (2.30 g, 5.14 mmol, 1.0 equiv.), n-BuLi (1.6 M in hexanes, 3.2 mL, 5.14 mmol, 1.0 equiv.) and 1-(naphthalen-2-yl)ethanone (1.22 g, 7.20 mmol, 1.4 equiv.), 0.71 g (54%) of the title compound as a yellow oil was obtained after purification by flash chromatography on $SiO_2$ (cyclohexane/EtOAc 995:5).

Odor description (dry-down of a 10% DPG solution after 24 hours on a smelling strip): floral, honey, orange flower, mimosa, acacia.

$^1$H-NMR (CDCl$_3$, 400 MHz): 7.86-7.17 (m, 12H), 6.18-6.13 (m, 0.35H), 5.79-5.75 (m, 0.65H), 3.65 (d, J=7.3 Hz, 0.7H), 3.39 (d, J=7.3 Hz, 1.3H), 2.28-2.27 (m, 1.05H), 2.19-2.18 (m, 1.95H).

MS (EI): 258 (M+, 94), 243 (65), 228 (20), 215 (12), 180 (27), 165 (100), 152 (30), 141 (16), 128 (28), 115 (68), 91 (52), 77 (13), 65 (6), 51 (11).

2.15 (4,8-Dimethylnona-2,7-dienyl)benzene

Starting from phenethyltriphenylphosphonium bromide (3.20 g, 7.15 mmol, 1.0 equiv.), n-BuLi (1.6 M in hexanes, 4.5 mL, 7.15 mmol, 1.0 equiv.) and 2,6-dimethylhept-5-enal (1.51 g, 10.7 mmol, 1.5 equiv.), 1.21 g (74%) of the title compound as a colorless oil was obtained after purification by flash chromatography on $SiO_2$ (cyclohexane/EtOAc 997:3).

$^1$H-NMR (CDCl$_3$, 400 MHz): 7.31-7.28 (m, 2H), 7.21-7.18 (m, 3H), 5.57-5.48 (m, 1H), 5.42-5.26 (m, 1H), 5.15-5.09 (m, 1H), 3.47-3.34 (m, 2H), 2.63-2.55 (m, 1H), 2.04-1.93 (m, 2H), 1.70 (d, J=1.3 Hz, 3H), 1.61 (s, 3H), 1.35-1.25 (m, 2H), 1.01 (d, J=6.6 Hz, 3H).

MS (EI): 228 (M+, 7), 213 (1), 185 (21), 157 (16), 143 (39), 137 (20), 129 (42), 117 (38), 109 (41), 104 (20), 91 (100), 81 (64), 69 (52), 55 (59), 41 (70).

2.16: 1-Methoxy-4-(3-phenylprop-1-enyl)benzene

Starting from phenethyltriphenylphosphonium bromide (3.16 g, 7.06 mmol, 1.0 equiv.), n-BuLi (1.6 M in hexanes, 4.4 mL, 7.06 mmol, 1.0 equiv.) and 4-methoxybenzaldehyde (1.44 g, 10.6 mmol, 1.5 equiv.), 1.36 g (86%) of the title compound as a light yellow oil was obtained after purification by flash chromatography on $SiO_2$ (cyclohexane/EtOAc 99:1).

Odor description (dry-down of a 10% DPG solution after 24 hours on a smelling strip): floral, aldehydic, anisic like, and honey, linden blossom.

$^1$H-NMR (CDCl$_3$, 400 MHz): 7.36-7.21 (m, 7H), 6.95-6.83 (m, 2H), 6.57-6.53 (m, 0.25H), 6.44-6.40 (m, 0.75H), 6.27-6.20 (m, 0.75H), 5.83-5.76 (m, 0.25H), 3.83 (s, 0.75H), 3.81 (s, 2.25H), 3.70 (dd, J=7.5, 1.4 Hz, 0.5H), 3.55 (d, J=7.1 Hz, 1.5H).

MS (EI): 224 (M+, 100), 209 (23), 193 (31), 178 (20), 165 (20), 121 (24), 115 (365), 103 (13), 91 (32), 77 (20), 65 (11), 51 (13).

2.17: 1-tert-Butyl-4-(2-methyl-5-phenylpent-3-enyl)benzene

Starting from phenethyltriphenylphosphonium bromide (3.00 g, 6.71 mmol, 1.0 equiv.), n-BuLi (1.6 M in hexanes, 4.2 mL, 6.71 mmol, 1.0 equiv.) and 3-(4-tert-butylphenyl)-2-methylpropanal (2.05 g, 10.1 mmol, 1.5 equiv.), 1.35 g (69%) of the title compound as a colorless oil was obtained after purification by flash chromatography on $SiO_2$ (cyclohexane/EtOAc 997:3).

Odor description (dry-down of a 10% DPG solution after 24 hours on a smelling strip): floral, green, muguet, watery, lilial like, and green, honey, aldehydic, syringe.

$^1$H-NMR (CDCl$_3$, 400 MHz): 7.33-6.99 (m, 9H), 5.62-5.59 (m, 0.1H), 5.49-5.47 (m, 0.1H), 5.46-5.39 (m, 0.9H), 5.36-5.31 (m, 0.9H), 3.31-3.13 (m, 2H), 2.89-2.80 (m, 1H), 2.62-2.54 (m, 2H), 1.31 (s, 9H), 1.03 (d, J=6.6 Hz, 3H).

MS (EI): 292 (M+, 8), 277 (3), 235 (4), 201 (8), 147 (100), 132 (19), 117 (44), 105 (15), 91 (39), 77 (6), 57 (33), 41 (11).

2.18: 1-(2,2-Dimethyl-5-phenylpent-3-enyl)-4-ethylbenzene

Starting from phenethyltriphenylphosphonium bromide (2.23 g, 4.98 mmol, 1.0 equiv.), n-BuLi (1.6 M in hexanes, 3.1 mL, 4.98 mmol, 1.0 equiv.) and 3-(4-ethylphenyl)-2,2-dimethylpropanal (1.42 g, 7.48 mmol, 1.5 equiv.), 0.71 g (51%) of the title compound as a colorless oil was obtained after purification by flash chromatography on $SiO_2$ (cyclohexane/EtOAc 997:3).

$^1$H-NMR (CDCl$_3$, 400 MHz): 7.30-7.10 (m, 9H), 5.47-5.38 (m, 2H), 3.44 (d, J=4.6 Hz, 1.4H), 3.39 (d, J=5.8 Hz, 0.6H), 2.81-2.63 (m, 4H), 1.28-1.18 (m, 9H).

MS (EI): 278 (M+, 2), 187 (39), 159 (77), 143 (20), 129 (14), 117 (100), 103 (10), 91 (54), 77 (10), 65 (8), 43 (9).

2.19: (5,7,7-Trimethyloct-2-enyl)benzene

Starting from phenethyltriphenylphosphonium bromide (2.80 g, 6.26 mmol, 1.0 equiv.), n-BuLi (1.6 M in hexanes, 3.9 mL, 6.26 mmol, 1.0 equiv.) and 3,5,5-trimethylhexanal (1.33 g, 9.39 mmol, 1.5 equiv.), 0.94 g (65%) of the title compound as a colorless oil was obtained after purification by flash chromatography on $SiO_2$ (cyclohexane/EtOAc 997:3).

Odor description (dry-down of a 10% DPG solution after 24 hours on a smelling strip): natural honey, woody aspects, dry strawberry aspects.

$^1$H-NMR (CDCl$_3$, 400 MHz): 7.31-7.28 (m, 2H), 7.21-7.18 (m, 3H), 5.66-5.46 (m, 2H), 3.41 (d, J=7.1 Hz, 1.7H), 3.36 (d, J=6.3 Hz, 0.3H), 2.19-1.98 (m, 2H), 1.68-1.57 (m, 1H), 1.36-1.27 (m, 1H), 1.14-1.05 (m, 1H), 1.00-0.85 (m, 12H).

MS (EI): 230 (M$^+$, 6), 174 (12), 132 (4), 117 (14), 104 (20), 91 (30), 57 (100), 41 (14).

2.20: (6-(6-Methylheptan-2-yloxy)hex-2-enyl)benzene

Starting from phenethyltriphenylphosphonium bromide (2.20 g, 4.92 mmol, 1.0 equiv.), n-BuLi (1.6 M in hexanes, 3.1 mL, 4.92 mmol, 1.0 equiv.) and 4-(6-methylheptan-2-yloxy) butanal (0.86 g, 4.29 mmol, 0.9 equiv.), 0.42 g (27%) of the title compound as a yellow oil was obtained after purification by flash chromatography on $SiO_2$ (cyclohexane/EtOAc 997:3).

$^1$H-NMR (CDCl$_3$, 400 MHz): 7.31-7.28 (m, 2H), 7.20-7.17 (m, 3H), 5.62-5.51 (m, 2H), 3.54-3.34 (m, 5H), 2.27-2.21 (m, 2H), 1.71-1.64 (m, 2H), 1.55-1.49 (m, 2H), 1.40-1.26 (m, 3H), 1.20-1.15 (m, 2H), 1.13 (d, J=6.1 Hz, 3H), 0.87 (d, J=6.6 Hz, 6H).

MS (EI): 288 (M$^+$, 1), 273 (1), 203 (8), 176 (6), 158 (31), 143 (24), 129 (73), 117 (67), 104 (17), 91 (100), 71 (40), 57 (56), 43 (40).

2.21 (5-(3-tert-Butylcyclohexyl)pent-2-enyl)benzene

Starting from phenethyltriphenylphosphonium bromide (2.60 g, 5.81 mmol, 1.0 equiv.), n-BuLi (1.3 M in hexanes, 4.5 mL, 5.81 mmol, 1.0 equiv.) and 3-(3-tert-butylcyclohexyl) propanal (1.45 g, 7.39 mmol, 1.3 equiv.), 1.01 g (61%) of the title compound as a colorless oil was obtained after purification by flash chromatography on $SiO_2$ (cyclohexane).

$^1$H-NMR (CDCl$_3$, 400 MHz): 7.31-7.28 (m, 2H), 7.21-7.17 (m, 3H), 5.61-5.48 (m, 2H),
3.42 (d, J=6.1 Hz, 1.7H), 3.34 (d, J=6.1 Hz, 0.3H), 2.24-2.04 (m, 2H), 1.83-1.73 (m, 4H), 1.49-1.15 (m, 4H), 1.02-0.54 (m, 13H).

MS (EI): 284 (M$^+$, 1), 269 (1), 227 (35), 192 (6), 145 (11), 137 (13), 131 (47), 117 (31), 104 (43), 91 (100), 81 (38), 67 (25), 57 (92), 41 (37).

2.22: (4-(4-tert-Pentylcyclohexyl)but-2-enyl)benzene

Starting from phenethyltriphenylphosphonium bromide (2.00 g, 4.47 mmol, 1.0 equiv.), n-BuLi (1.6 M in hexanes, 2.8 mL, 4.47 mmol, 1.0 equiv.) and 2-(4-tert-pentylcyclohexyl) acetaldehyde (1.32 g, 6.71 mmol, 1.5 equiv.), 0.62 g (48%) of the title compound as a colorless oil was obtained after purification by flash chromatography on $SiO_2$ (cyclohexane).

$^1$H-NMR (CDCl$_3$, 400 MHz): 7.33-7.28 (m, 2H), 7.22-7.17 (m, 3H), 5.63-5.48 (m, 2H), 3.44-3.34 (m, 2H), 2.21-2.02 (m, 2H), 1.91-1.64 (m, 4H), 1.49-1.41 (m, 2H), 1.30-1.20 (m, 2H), 1.18-0.88 (m, 4H), 0.81-0.74 (m, 9H).

MS (EI): 284 (M$^+$, 4), 269 (1), 255 (11), 214 (11), 131 (21), 117 (26), 104 (33), 97 (23), 91 (51), 83 (17), 71 (100), 55 (28), 43 (47).

EXAMPLE 3

2-Ethoxy-4-(3-phenylprop-1-enyl)phenol a) Phenethyltriphenylphosphonium bromide (4.74 g, 10.6 mmol, 1.0 equiv.) in THF (20 mL), was cooled to 0° C. After adding n-BuLi (1.6 M in hexanes, 6.6 mL, 10.6 mmol, 1.0 equiv.) at 0° C., the red solution was stirred at 70° C. for 1 h. The mixture was re-cooled to 0° C., 4-(tert-butyldimethylsilyloxy)-3-ethoxybenzaldehyde) (2.98 g, 10.6 mmol, 1.0 equiv.) in THF (10 mL) was added, and the mixture was stirred at 70° C. for 14 h. After addition of $H_2O$, the aqueous layer was extracted with cyclohexane (2×), the combined organic phases were washed with brine, dried (MgSO$_4$), filtered and the filtrate was concentrated. The residue was purified by flash chromatography on $SiO_2$ (cyclohexane/EtOAc 98:2) to yield 3.12 g (80%) of a yellow oil, containing tert-butyl(2-ethoxy-4-(3-phenylprop-1-enyl)phenoxy)-dimethylsilane.

b) To a solution of tert-butyl(2-ethoxy-4-(3-phenylprop-1-enyl)phenoxy)-dimethylsilane (3.12 g, 8.46 mmol, 1.0 equiv.), in THF (17 mL), n-Bu$_4$NF (10.2 mL, 10.2 mmol, 1.2 equiv., 1.0 M in THF) was added, and the mixture was stirred at 25° C. for 1 h. After addition of $H_2O$, the aqueous layer was extracted with MTBE (2×), the combined organic phases were washed with brine, dried (MgSO$_4$), filtered and the filtrate was concentrated. The residue was purified by flash chromatography on $SiO_2$ (cyclohexane/EtOAc 95:5) to yield 1.60 g (74%) of the title compound as a yellow oil.

Odor description (dry-down of a 10% DPG solution after 24 hours on a smelling strip): floral, spicy, vanilla, green, honey.

$^1$H-NMR (CDCl$_3$, 400 MHz): 7.36-7.30 (m, 2H), 7.28-7.23 (m, 3H), 6.98-6.79 (m, 3H), 6.54-6.50 (m, 0.4H), 6.40-6.35 (m, 0.6H), 6.22-6.15 (m, 0.6H), 5.82-5.75 (m, 0.4H), 5.70 (s, 0.4H), 5.68 (s, 0.6H), 4.11 (q, J=7.1 Hz, 1.2H), 4.05 (q, J=7.0 Hz, 0.8H), 3.69 (dd, J=7.6, 1.3 Hz, 0.8H), 3.53 (d, J=6.8 Hz, 1.2H), 1.44 (t, J=7.1 Hz, 1.8H), 1.42 (t, J=7.1 Hz, 1.2H).

MS (EI): 254 (M$^+$, 100), 237 (2), 225 (26), 207 (23), 197 (10), 179 (26), 165 (17), 152 (11), 131 (13), 115 (46), 103 (13), 91 (41), 77 (15), 65 (11).

EXAMPLE 4.1-4.3

Following the general procedure as described in Example 3 the following compounds have been prepared:

4.1: 4-(3-Methyl-5-phenylpent-3-enyl)phenol a) First starting from phenethyltriphenylphosphonium bromide (5.27 g, 11.8 mmol, 1.0 equiv.), n-BuLi (1.6 M in hexanes, 7.4 mL, 11.8 mmol, 1.0 equiv.) and 4-(4-(tert-butyldimethylsilyloxy)phenyl)butan-2-one (3.94 g, 14.1 mmol, 1.2 equiv.), 1.86 g (43%) of a light yellow oil, containing tert-butyldimethyl(4-(3-methyl-5-phenylpent-3-enyl)phenoxy)silane, was obtained after purification by flash chromatography on $SiO_2$ (hexanes/EtOAc 99:1).

b) Starting from tert-butyldimethyl(4-(3-methyl-5-phenylpent-3-enyl)phenoxy)silane (1.86 g, 5.07 mmol, 1.0 equiv.) and n-Bu$_4$NF (6.1 mL, 6.09 mmol, 1.2 equiv., 1.0 M in THF), 0.78 g (61%) of the title compound as a light yellow oil was obtained after purification by flash chromatography on SiO$_2$ (hexanes/EtOAc 95:5→9:1).

$^1$H-NMR (CDCl$_3$, 400 MHz): 7.33-7.28 (m, 2H), 7.24-7.19 (m, 1H), 7.16-7.06 (m, 4H), 6.80-6.75 (m, 2H), 5.41-5.35 (m, 1H), 4.92 (d, J=7.6 Hz, 1H), 3.39 (d, J=7.3 Hz, 1H), 3.28 (d, J=7.3 Hz, 1H), 2.74-2.68 (m, 2H), 2.46-2.42 (m, 1H), 2.37-2.33 (m, 1H), 1.82 (q, J=1.8 Hz, 1.5H), 1.79 (d, J=0.5 Hz, 1.5H).

MS (EI): 252 (M$^+$, 11), 145 (4), 129 (5), 107 (100), 103 (2), 91 (9), 77 (10).

4.2: 2-Ethoxy-4-(3-p-tolylprop-1-enyl)phenol a) Starting from p-methylphenethyltriphenylphosphonium bromide (3.90 g, 8.45 mmol, 1.0 equiv.), n-BuLi (1.6 M in hexanes, 5.3 mL, 8.45 mmol, 1.0 equiv.) and 4-(tert-butyldimethylsilyloxy)-3-ethoxybenzaldehyde (2.37 g, 8.45 mmol, 1.0 equiv.), 2.72 g (84%) of a light yellow oil, containing (E)-tert-butyl(2-ethoxy-4-(3-p-tolylprop-1-enyl)phenoxy)dimethylsilane, was obtained after purification by flash chromatography on SiO$_2$ (hexanes/EtOAc 997:3).

b) Starting from (E)-tert-butyl(2-ethoxy-4-(3-p-tolylprop-1-enyl)phenoxy)dimethylsilane (2.72 g, 7.11 mmol, 1.0 equiv.) and n-Bu$_4$NF (8.5 mL, 8.53 mmol, 1.2 equiv., 1.0 M in THF), 1.53 g (80%) of the title compound as a viscous yellow oil was obtained after purification by flash chromatography on SiO$_2$ (hexanes/EtOAc 19:1→9:1).

Odor description (dry-down of a 10% DPG solution after 24 hours on a smelling strip): powdery vanilla, floral, slightly spicy, carnation.

$^1$H-NMR (CDCl$_3$, 400 MHz): 7.19-7.09 (m, 4H), 6.95-6.81 (m, 3H), 6.51-6.48 (m, 0.35H), 6.39-6.34 (m, 0.65H), 6.21-6.13 (m, 0.65H), 5.80-5.74 (m, 0.35H), 5.66 (s, 0.35H), 5.63 (s, 0.65H), 4.11 (q, J=7.1 Hz, 1.3H), 4.06 (q, J=7.1 Hz, 0.7H), 3.65 (dd, J=7.5, 1.4 Hz, 0.7H), 3.49 (dd, J=7.1, 1.0 Hz, 1.3H), 2.34 (s, 3H), 1.47-1.41 (m, 3H).

MS (EI): 268 (M$^+$, 100), 253 (9), 239 (19), 223 (17), 207 (20), 193 (15), 178 (22), 165 (18), 152 (12), 129 (32), 115 (26), 105 (30), 91 (23), 77 (17), 65 (11), 55 (10), 29 (14).

4.3: 2-Ethoxy-4-(3-(4-methoxyphenyl)prop-1-enyl)phenol a) First starting from p-methoxyphenethyltriphenylphosphonium bromide (3.90 g, 8.17 mmol, 1.0 equiv.), n-BuLi (1.6 M in hexanes, 5.1 mL, 8.17 mmol, 1.0 equiv.) and 4-(tert-butyldimethylsilyloxy)-3-ethoxybenzaldehyde (2.29 g, 8.17 mmol, 1.0 equiv.), 2.50 g (77%) of a yellow oil, containing (E)-tert-butyl(2-ethoxy-4-(3-(4-methoxyphenyl)prop-1-enyl)phenoxy)dimethylsilane, was obtained after purification by flash chromatography on SiO$_2$ (hexanes/EtOAc 99:1).

b) Then, starting from (E)-tert-butyl(2-ethoxy-4-(3-(4-methoxyphenyl)prop-1-enyl)phenoxy)dimethylsilane (2.50 g, 6.27 mmol, 1.0 equiv.) and n-Bu$_4$NF (7.5 mL, 7.53 mmol, 1.2 equiv., 1.0 M in THF), 1.25 g (70%) of the title compound as a viscous yellow oil was obtained after purification by flash chromatography on SiO$_2$ (hexanes/EtOAc 19:1→9:1).

$^1$H-NMR (CDCl$_3$, 400 MHz): 7.19-7.13 (m, 2H), 6.95-6.81 (m, 5H), 6.51-6.47 (m, 0.35H), 6.37-6.33 (m, 0.65H), 6.20-6.13 (m, 0.65H), 5.79-5.72 (m, 0.35H), 5.67 (s, 0.35H), 5.64 (s, 0.65H), 4.11 (q, J=6.8 Hz, 1.3H), 4.06 (q, J=7.1 Hz, 0.7H), 3.80-3.80 (m, 3H), 3.63 (dd, J=7.3, 1.5 Hz, 0.7H), 3.47 (d, J=6.6 Hz, 1.3H), 1.47-1.41 (m, 3H).

MS (EI): 284 (M$^+$, 100), 267 (5), 255 (22), 239 (19), 227 (11), 209 (11), 195 (9), 165 (18), 145 (35), 134 (18), 121 (45), 115 (19), 103 (10), 91 (23), 77 (22), 65 (10), 55 (11), 29 (16).

EXAMPLE 5

1-Methoxy-4-(4-nnethyltridec-2-enyl)benzene p-Methoxyphenethyltriphenylphosphonium bromide (3.40 g, 7.12 mmol, 1.0 equiv.) in THF (14 mL), was cooled to 0° C. After adding n-BuLi (1.6 M in hexanes, 4.5 mL, 7.12 mmol, 1.0 equiv.) at 0° C., the red solution was stirred at 65° C. for 1 h. The mixture was re-cooled to 0° C., 2-methylundecanal (1.97 g, 10.7 mmol, 1.5 equiv.) in THF (6 mL) was added, and the mixture was stirred at 70° C. for 14 h. After addition of H$_2$O, the aqueous layer was extracted with cyclohexane (2×), the combined organic phases were washed with brine, dried (MgSO$_4$), filtered and the filtrate was concentrated. The residue was purified by flash chromatography on SiO$_2$ (cyclohexane/EtOAc 98:2) to yield 1.36 g (63%) of the title compound as a light yellow oil.

$^1$H-NMR (CDCl$_3$, 400 MHz): 7.13-7.09 (m, 2H), 6.85-6.82 (m, 2H), 5.49-5.43 (m, 1H), 5.28-5.22 (m, 1H), 3.79 (s, 3H), 3.40-3.26 (m, 2H), 2.58-2.50 (m, 1H), 1.33-1.25 (m, 16H), 0.98 (d, J=6.6 Hz, 3H), 0.89 (t, J=6.8 Hz, 3H).

MS (EI): 302 (M$^+$, 13), 194 (3), 175 (10), 147 (100), 134 (50), 121 (71), 108 (11), 91 (9), 82 (10), 67 (5), 55 (9), 41 (12).

EXAMPLE 6.1-6.4

Following the general procedure as described in Example 5 the following compounds have been prepared:

6.1: 1-Isopropyl-3-(6-(4-methoxyphenyl)hex-4-en-2-yl)benzene

Starting from p-methoxyphenethyltriphenylphosphonium bromide (1.20 g, 2.51 mmol, 1.0 equiv.), n-BuLi (1.6 M in hexanes, 1.6 mL, 2.51 mmol, 1.0 equiv.) and 3-(3-isopropylphenyl)butanal (0.72 g, 3.77 mmol, 1.5 equiv.), 0.20 g (26%) of the title compound as a yellow oil was obtained after purification by flash chromatography on SiO$_2$ (cyclohexane/EtOAc 99:1).

$^1$H-NMR (CDCl$_3$, 400 MHz): 7.25-7.21 (m, 1H), 7.10-6.98 (m, 5H), 6.83-6.79 (m, 2H), 5.55-5.43 (m, 2H), 3.79 (s, 3H), 3.27 (d, J=7.1 Hz, 1.6H), 3.23 (d, J=6.3 Hz, 0.4H), 2.93-2.86 (m, 1H), 2.83-2.76 (m, 1H), 2.47-2.37 (m, 2H), 1.31 (d, J=7.1 Hz, 3H), 1.27-1.22 (m, 6H).

MS (EI): 308 (M$^+$, 16), 161 (9), 147 (100), 131 (6), 121 (19), 105 (21), 91 (17), 77 (16), 43 (19).

6.2: 1-((6E)-Dodeca-2,6-dienyl)-4-methoxybenzene

Starting from p-methoxyphenethyltriphenylphosphonium bromide (3.12 g, 6.54 mmol, 1.0 equiv.), n-BuLi (1.6 M in hexanes, 4.1 mL, 6.54 mmol, 1.0 equiv.) and (E)-dec-4-enal (1.51 g, 9.80 mmol, 1.5 equiv.), 0.85 g (48%) of the title compound as a colorless oil was obtained after purification by flash chromatography on SiO$_2$ (hexanes/EtOAc 992:8).

Odor description (dry-down of a 10% DPG solution after 24 hours on a smelling strip): aldehydic, green, watery, floral, anisic.

$^1$H-NMR (CDCl$_3$, 400 MHz): 7.13-7.09 (m, 2H), 6.85-6.81 (m, 2H), 5.56-5.39 (m, 4H), 3.79 (s, 3H), 3.34 (d, J=6.6 Hz, 1.7H), 3.27 (d, J=5.8 Hz, 0.3H), 2.22-1.96 (m, 6H), 1.35-1.25 (m, 6H), 0.91-0.87 (m, 3H).

MS (EI): 272 (M+, 7), 173 (7), 161 (32), 147 (19), 134 (100), 129 (14), 121 (51), 91 (21), 77 (9), 69 (11), 55 (16), 41 (21).

6.3: 2-(4-(4-Methoxyphenyl)but-2-en-2-yl)naphthalene

Starting from p-methoxyphenethyltriphenylphosphonium bromide (3.15 g, 6.60 mmol, 1.0 equiv.), n-BuLi (1.6 M in hexanes, 4.2 mL, 6.60 mmol, 1.0 equiv.) and 1-(naphthalen-2-yl)ethanone (1.69 g, 9.90 mmol, 1.5 equiv.), 0.92 g (48%) of the title compound as a yellow oil was obtained after purification by flash chromatography on $SiO_2$ (hexanes/EtOAc 995:5→99:1).

Odor description (dry-down of a 10% DPG solution after 24 hours on a smelling strip): floral, orange flower, natural, cassie.

$^1$H-NMR (CDCl$_3$, 400 MHz): 7.86-7.39 (m, 7H), 7.23-7.19 (m, 0.8H), 7.11-7.07 (m, 1.2H), 6.90-6.82 (m, 2H), 6.16-6.11 (m, 0.4H), 5.77-5.72 (m, 0.6H), 3.81 (s, 1.2H), 3.80 (s, 1.8H), 3.59 (d, J=7.3 Hz, 0.8H), 3.33 (d, J=7.3 Hz, 1.2H), 2.27-2.26 (m, 1.2H), 2.18-2.17 (m, 1.8H).

MS (EI): 288 (M+, 79), 273 (55), 258 (8), 215 (12), 180 (39), 165 (100), 152 (27), 145 (48), 128 (20), 121 (54), 115 (22), 91 (16), 77 (15), 65 (7), 51 (7).

6.4: 1-tert-Butyl-4-(5-(4-methoxyphenyl)-2-methylpent-3-enyl)benzene

Starting from p-methoxyphenethyltriphenylphosphonium bromide (3.10 g, 6.49 mmol, 1.0 equiv.), n-BuLi (1.6 M in hexanes, 4.1 mL, 6.49 mmol, 1.0 equiv.) and 3-(4-tert-butylphenyl)-2-methylpropanal (1.99 g, 9.74 mmol, 1.5 equiv.), 1.07 g (44%) of the title compound as a light yellow oil was obtained after purification by flash chromatography on $SiO_2$ (cyclohexane/EtOAc 997:3).

$^1$H-NMR (CDCl$_3$, 400 MHz): 7.32-7.29 (m, 2H), 7.13-7.10 (m, 2H), 6.94-6.91 (m, 2H), 6.79-6.76 (m, 2H), 5.47-5.31 (m, 2H), 3.77 (s, 3H), 3.23-3.09 (m, 2H), 2.90-2.83 (m, 1H), 2.60-2.57 (m, 2H), 1.33 (s, 9H), 1.04 (d, J=6.6 Hz, 3H).

MS (EI): 322 (M+, 26), 201 (34), 175 (100), 160 (12), 147 (83), 134 (25), 121 (100), 105 (12), 91 (26), 77 (9), 57 (14), 41 (11).

EXAMPLE 7

1-Methyl-4-(4-methyltridec-2-enyl)benzene p-Methylphenethyltriphenylphosphonium bromide (2.90 g, 6.29 mmol, 1.0 equiv.) in THF (12 mL), was cooled to 0° C. After adding n-BuLi (1.6 M in hexanes, 3.9 mL, 6.29 mmol, 1.0 equiv.) at 0° C., the red solution was stirred at 65° C. for 1 h. The mixture was re-cooled to 0° C., 2-methylundecanal (1.74 g, 9.43 mmol, 1.5 equiv.) in THF (5 mL) was added, and the mixture was stirred at 65° C. for 16 h. After addition of $H_2O$, the aqueous layer was extracted with cyclohexane (2×), the combined organic phases were washed with brine, dried (MgSO$_4$), filtered and the filtrate was concentrated. The residue was purified by flash chromatography on SiO$_2$ (cyclohexane/EtOAc 997:3) to yield 1.24 g (69%) of the title compound as a colorless oil.

Odor description (dry-down after 24 hours on a smelling strip): fresh, clean, aldehydic, resinous.

$^1$H-NMR (CDCl$_3$, 400 MHz): 7.13-7.07 (m, 4H), 5.50-5.44 (m, 1H), 5.29-5.23 (m, 1H), 3.42-3.29 (m, 2H), 2.57-2.53 (m, 1H), 2.32 (s, 3H), 1.33-1.21 (m, 16H), 0.98 (d, J=6.8 Hz, 3H), 0.91-0.87 (m, 3H).

MS (EI): 286 (M+, 8), 159 (21), 131 (82), 118 (100), 105 (62), 91 (9), 83 (7), 69 (14), 55 (18), 41 (21).

EXAMPLE 8.1-8.3

Following the general procedure as described in Example 7 the following compounds have been prepared:

8.1: 1-((6E)-Dodeca-2,6-dienyl)-4-methylbenzene

Starting from p-methylphenethyltriphenylphosphonium bromide (2.90 g, 6.29 mmol, 1.0 equiv.), n-BuLi (1.6 M in hexanes, 3.9 mL, 6.29 mmol, 1.0 equiv.) and (E)-dec-4-enal (1.45 g, 9.43 mmol, 1.5 equiv.), 0.92 g (57%) of the title compound as a colorless oil was obtained after purification by flash chromatography on SiO$_2$ (cyclohexane/EtOAc 997:3).

Odor description (dry-down of a 10% DPG solution after 24 hours on a smelling strip): aldehydic, green, sharp, watery.

$^1$H-NMR (CDCl$_3$, 400 MHz): 7.13-7.07 (m, 4H), 5.60-5.40 (m, 4H), 3.37 (d, J=6.8 Hz, 1.7H), 3.30 (d, J=6.1 Hz, 0.3H), 2.33 (s, 3H), 2.25-1.98 (m, 6H), 1.39-1.25 (m, 6H), 0.92-0.88 (m, 3H).

MS (EI): 256 (M+, 2), 241 (1), 185 (3), 145 (58), 129 (45), 118 (100), 105 (58), 91 (17), 79 (11), 69 (22), 55 (22), 41 (26).

8.2: 1-tert-Butyl-4-(2-methyl-5-p-tolylpent-3-enyl)benzene

Starting from p-methylphenethyltriphenylphosphonium bromide (5.04 g, 9.91 mmol, 1.0 equiv.), n-BuLi (1.6 M in hexanes, 6.2 mL, 9.91 mmol, 1.0 equiv.) and 3-(4-tert-butylphenyl)-2-methylpropanal (3.04 g, 14.9 mmol, 1.5 equiv.), 1.26 g (42%) of the title compound as a light yellow oil was obtained after purification by flash chromatography on SiO$_2$ (cyclohexane/EtOAc 997:3).

$^1$H-NMR (CDCl$_3$, 400 MHz): 7.34-7.30 (m, 2H), 7.15-7.11 (m, 2H), 7.07 (d, J=7.8 Hz, 2H), 6.94 (d, J=8.0 Hz, 2H), 5.51-5.33 (m, 2H), 3.31-3.13 (m, 2H), 2.93-2.86 (m, 1H), 2.62-2.55 (m, 2H), 2.33 (s, 3H), 1.36 (s, 9H), 1.06 (d, J=6.7 Hz, 3H).

MS (EI): 306 (M+, 16), 291 (2), 249 (2), 201 (11), 159 (95), 147 (100), 131 (36), 117 (44), 105 (50), 91 (28), 77 (9), 57 (55), 41 (13).

8.3: 5-(3-p-Tolylprop-1-enyl)benzo[d][1,3]dioxole

Starting from p-methylphenethyltriphenylphosphonium iodide, which has been synthesized from 1-(2-iodoethyl)-4-methylbenzene and PPh3, (2.54 g, 5.00 mmol, 1.0 equiv.), n-BuLi (1.6 M in hexanes, 3.1 mL, 5.00 mmol, 1.0 equiv.) and benzo[d][1,3]dioxole-5-carbaldehyde (0.98 g, 6.50 mmol, 1.3 equiv.), 0.50 g (40%) of the title compound as a light yellow oil was obtained after purification by flash chromatography on SiO$_2$ (cyclohexane/EtOAc 997:3).

$^1$H-NMR (CDCl$_3$, 400 MHz): 7.14-7.11 (m, 4H), 6.91-6.73 (m, 3H), 6.48 (dt, J=11.5, 1.6 Hz, 0.3H), 6.37 (d, J=15.7 Hz, 0.7H), 6.18 (dt, J=15.7, 6.8 Hz, 0.7H), 5.96 (s, 0.6H), 5.94 (s, 1.4H), 5.77 (dt, J=11.4, 7.6 Hz, 0.3H), 3.63 (dd, J=7.5, 1.6 Hz, 0.6H), 3.49 (dd, J=6.9, 1.1 Hz, 1.4H), 2.34 (s, 3H).

MS (EI): 252 (M+, 100), 237 (31), 222 (20), 207 (35), 193 (12), 179 (38), 165 (12), 152 (11), 135 (13), 129 (14), 115 (27), 103 (20), 89 (18), 77 (26), 63 (12), 51 (12).

EXAMPLE 9

2-(4-Methyltridec-2-enyl)naphthalene

A solution of naphthaleneethyltriphenylphosphonium bromide which has been synthesized from 2-(2-bromoethyl)-2- naphthalene and PPh3, (3.36 g, 6.76 mmol, 1.0 equiv.) in THF (14 mL), was cooled to 0° C. After adding n-BuLi (1.6 M in hexanes, 4.2 mL, 6.76 mmol, 1.0 equiv.) at 0° C., the red-brown suspension was stirred at 65° C. for 1 h. The mixture was re-cooled to 0° C., 2-methylundecanal (1.87 g, 10.1 mmol, 1.5 equiv.) in THF (5 mL) was added, and the mixture was stirred at 65° C. for 16 h. After addition of $H_2O$, the aqueous layer was extracted with cyclohexane (2×), the combined organic phases were washed with brine, dried ($MgSO_4$), filtered and the filtrate was concentrated. The residue was purified by flash chromatography on $SiO_2$ (cyclohexane) to yield 0.31 g (14%) of the title compound as a light yellow oil.

$^1$H-NMR ($CDCl_3$, 400 MHz): 7.84-7.35 (m, 7H), 7.37-7.35 (m, 1H), 5.63-5.57 (m, 1H), 5.39-5.33 (m, 1H), 3.64-3.51 (m, 2H), 2.68-2.60 (m, 1H), 1.39-1.25 (m, 16H), 1.04 (d, J=6.6 Hz, 3H), 0.91 (t, J=6.8 Hz, 3H).

MS (EI): 322 ($M^+$, 26), 196 (2), 179 (18), 167 (73), 154 (100), 141 (90), 128 (50), 115 (14), 95 (11), 82 (17), 69 (12), 55 (20), 43 (22).

EXAMPLE 10

(3-Methyldodec-1-enyl)benzene

A suspension of benzyltriphenylphosphonium bromide (3.20 g, 7.38 mmol, 1.0 equiv.) in THF (14 mL), was cooled to 0° C. After adding n-BuLi (1.6 M in hexanes, 4.6 mL, 7.38 mmol, 1.0 equiv.) at 0° C., the red suspension was stirred at 65° C. for 1 h. The mixture was re-cooled to 0° C., 2-methylundecanal (2.04 g, 11.1 mmol, 1.5 equiv.) in THF (5 mL) was added, and the mixture was stirred at 65° C. for 18 h. After addition of $H_2O$, the aqueous layer was extracted with cyclohexane (2×), the combined organic phases were washed with brine, dried ($MgSO_4$), filtered and the filtrate was concentrated. The residue was purified by flash chromatography on $SiO_2$ (cyclohexane) to yield 1.45 g (76%) of the title compound as a colorless oil.

$^1$H-NMR ($CDCl_3$, 400 MHz): 7.37-7.17 (m, 5H), 6.39-6.32 (m, 1H), 6.10 (dd, J=15.9, 7.8 Hz, 0.7H), 6.10 (dd, J=11.6, 10.4 Hz, 0.3H), 2.79-2.69 (m, 0.3H), 2.34-2.24 (m, 0.7H), 1.41-1.23 (m, 16H), 1.08 (d, J=6.8 Hz, 2.1H), 1.04 (d, J=6.6 Hz, 0.9H), 0.89 (t, J=6.8 Hz, 3H).

MS (EI): 258 ($M^+$, 7), 243 (1), 131 (100), 115 (8), 104 (26), 91 (26), 55 (4), 41 (8).

EXAMPLE 11

4-(3-Methyl-4-phenylbut-3-enyl)phenol

To a suspension of benzyltriphenylphosphonium bromide (10.9 g, 25.1 mmol, 1.2 equiv.) in THF (35 mL), was added potassium-t-amylat (1.7 M in toluene, 20 mL, 34.0 mmol, 1.7 equiv.) at 25° C. 4-(4-Hydroxyphenyl)butan-2-one (3.3 g, 20.1 mmol, 1.0 equiv.) in THF (5 mL) was added to the red suspension, and the mixture was stirred at 70° C. for 30 min. After addition of 20% aq. AcOH-solution (10 mL) at 25° C., the aqueous layer was diluted with hexanes (50 mL). The organic phase was washed with $H_2O$ (2×30 mL) and MeOH/$H_2O$ (8:2, 2×20 mL) and concentrated. The residue was purified by flash chromatography on $SiO_2$ to yield 2.10 g (44%) of the title compound as a white solid.

$^1$H-NMR ($CDCl_3$, 400 MHz): 7.31-7.25 (m, 2H), 7.20-7.11 (m, 3H), 7.07-7.04 (m, 1.2H), 7.00-6.97 (m, 0.8H), 6.75-6.68 (m, 2H), 6.31 (s, 0.4H), 6.23 (s, 0.6H), 5.09 (s, 1H), 2.76-2.69 (m, 2H), 2.49-2.45 (m, 0.8H), 2.43-2.39 (m, 1.2H), 1.91 (d, J=1.3 Hz, 1.2H), 1.87 (d, J=1.3 Hz, 1.8H).

MS (EI): 238 ($M^+$, 9), 131 (23), 115 (11), 107 (100), 91 (17), 77 (13).

EXAMPLE 12

2-Ethoxy-4-(4-(4-hydroxyphenyl)-2-methylbut-1-enyl)phenol a) To a solution of 4-(tert-butyldimethylsilyloxy)-3-ethoxybenzaldehyde (12.7 g, 45.4 mmol, 1.0 equiv.) in EtOH (50 mL), $NaBH_4$ (868 mg, 22.7 mmol, 0.5 equiv.) was added at 0° C., and the mixture was stirred at 0° C. for 2 h. After slow addition of sat. aq. $NaHCO_3$-solution, the aqueous layer was extracted with EtOAc (2×). The combined organic phases were washed with brine, dried ($MgSO_4$), filtered and the filtrate was concentrated to yield 12.6 g (98%) of (4-(tert-butyldimethylsilyloxy)-3-ethoxyphenyl)methanol as a light yellow oil.

b) To a solution of (4-(tert-butyldimethylsilyloxy)-3-ethoxyphenyl)methanol (12.5 g, 44.4 mmol, 1.0 equiv.) in $CH_2Cl_2$ (45 mL), $PBr_3$ (5.0 mL, 53.2 mmol, 1.2 equiv.) was added at 0° C., and the mixture was stirred at 0° C. for 30 min. After slow addition of sat. aq. $NaHCO_3$-solution, the aqueous layer was extracted with $CH_2Cl_2$ (2×). The combined organic phases were washed with brine, dried ($MgSO_4$), filtered and the filtrate was concentrated to yield 14.5 g (94%) of (4-(bromomethyl)-2-ethoxyphenoxy)(tert-butyl)dimethylsilane as a light yellow oil.

c) To a solution of (4-(bromomethyl)-2-ethoxyphenoxy)(tert-butyl)dimethylsilane (14.5 g, 41.8 mmol, 1.0 equiv.) in toluene (84 mL), $PPh_3$ (11.0 g, 41.8 mmol, 1.0 equiv.) was added. The mixture was stirred at 25° C. for 20 h and concentrated to yield 25.1 g (99%) of (4-(tert-Butyldimethylsilyloxy)-3-ethoxyphenyl)methyltriphenylphosphonium bromide as a white solid.

d) A solution of (4-(tert-Butyldimethylsilyloxy)-3-ethoxyphenyl)methyltriphenyl-phosphonium bromide (28.7 g, 41.6 mmol, 1.0 equiv.) in THF (90 mL), was cooled to 0° C. After adding n-BuLi (1.6 M in hexanes, 26 mL, 41.6 mmol, 1.0 equiv.) at 0° C., the red suspension was stirred at 0° C. for 15 min. 4-(4-(Tert-butyldimethylsilyloxy)phenyl)butan-2-one (12.9 g, 41.6 mmol, 1.0 equiv.) in THF (30 mL) was added, and the mixture was stirred at 0° C.→70° C. for 16 h. After addition of $H_2O$ at 25° C., the aqueous layer was extracted with hexanes (2×), the combined organic phases were washed with brine, dried ($MgSO_4$), filtered and the filtrate was concentrated. The residue was purified by flash chromatography on $SiO_2$ (cyclohexane/EtOAc 98:2) to give tert-butyl(4-(4-(4-((tert-butyldimethylsilyl)oxy)-3-ethoxyphenyl)-3-methylbut-3-en-1-yl)phenoxy)dimethylsilane as a colorless oil.

e) tert-Butyl(4-(4-(4-((tert-butyldimethylsilyl)oxy)-3-ethoxyphenyl)-3-methylbut-3-en-1-yl)phenoxy)dimethylsilane was dissolved in THF (30 mL), n-$Bu_4NF$ (30 mL, 30.0 mmol, 0.7 equiv., 1.0 M in THF) was added, and the mixture was stirred at 25° C. for 1 h. After addition of $H_2O$, the aqueous layer was extracted with MTBE (2×), the combined organic phases were washed with brine, dried ($MgSO_4$), filtered and the filtrate was concentrated. The residue was purified by flash chromatography on $SiO_2$ (cyclohexane/EtOAc 9:1→4:1) to yield 5.87 g (48% over 2 steps) of the title compound as a light yellow oil.

Odor description (dry-down of a 10% DPG solution after 24 hours on a smelling strip): sweet, raspberry, vanillin, plumy.

$^1$H-NMR ($CDCl_3$, 400 MHz): 7.10-7.07 (m, 1.12H), 7.04-7.00 (m, 0.88H), 6.88 (d, J=8.1 Hz, 0.56H), 6.85 (d, J=8.1 Hz, 0.44H), 6.79-6.61 (m, 4H), 6.24 (s, 0.44H), 6.17 (s, 0.56H), 5.64 (s, 0.56H), 5.63 (s, 0.44H), 4.82 (d, J=2.0 Hz, 1H), 4.11 (q, J=7.0 Hz, 1.12H), 4.02 (q, J=7.0 Hz, 0.88H), 2.77-2.71 (m, 2H), 2.52-2.48 (m, 0.88H), 2.43-2.39 (m, 1.12H), 1.91 (d, J=1.4 Hz, 1.32H), 1.89 (d, J=1.3 Hz, 1.68H), 1.45 (t, J=7.0 Hz, 1.68H), 1.41 (t, J=7.0 Hz, 1.32H).

MS (EI): 298 (M$^+$, 10), 191 (16), 163 (3), 145 (100), 117 (14), 107 (26), 91 (8), 77 (11).

EXAMPLE 13

2-Ethoxy-4-(4-(3-isopropylphenyl)pent-1-enyl)phenol (4-(tert-Butyldimethylsilyloxy)-3-ethoxyphenyl)methyltriphenylphosphonium bromide (1.15 g, 1.89 mmol, 1.0 equiv.) in THF (8 mL), was cooled to 0° C. After adding n-BuLi (1.6 M in hexanes, 1.2 mL, 1.89 mmol, 1.0 equiv.) at 0° C., the red solution was stirred at 65° C. for 1 h. The mixture was re-cooled to 0° C., 3-(3-isopropylphenyl)butanal (541 mg, 2.84 mmol, 1.5 equiv.) in THF (3 mL) was added, and the mixture was stirred at 65° C. for 18 h. After addition of H$_2$O, the aqueous layer was extracted with cyclohexane (2x), the combined organic phases were washed with brine, dried (MgSO$_4$), filtered and the filtrate was concentrated. The residue was purified by flash chromatography on SiO$_2$ (cyclohexane/EtOAc 98:2) to yield a colorless oil which was dissolved in THF (10 mL). n-Bu$_4$NF (1.0 M in THF, 2.3 mL, 2.27 mmol, 1.2 equiv.) was added, and the mixture was stirred at 25° C. for 1 h. After addition of H$_2$O, the aqueous layer was extracted with EtOAc (2x), the combined organic phases were washed with brine, dried (MgSO$_4$), filtered and the filtrate was concentrated. The residue was purified by flash chromatography on SiO$_2$ (cyclohexane/EtOAc 19:1→9:1) to yield 0.33 g (54% over 2 steps) of the title compound as a yellow oil.

1H-NMR (CDCl$_3$, 400 MHz): 7.27-7.21 (m, 1H), 7.08-7.02 (m, 3H), 6.89-6.74 (m, 3H), 6.35-6.28 (m, 1H), 5.98 (ddd, J=15.7, 7.8, 6.6 Hz, 0.6H), 5.65 (s, 0.4H), 5.63 (s, 0.6H), 5.52 (dt, J=11.8, 7.1 Hz, 0.4H), 4.16-4.05 (m, 2H), 2.93-2.80 (m, 2H), 2.64-2.35 (m, 2H), 1.46-1.42 (m, 3H), 1.31-1.24 (m, 9H).

MS (EI): 324 (M$^+$, 6), 177 (36), 147 (11), 131 (100), 117 (5), 103 (23), 91 (10), 77 (6), 43 (12).

EXAMPLE 14.1-14.2

Following the general procedure as described in Example 13 the following compounds have been prepared:

14.1: 2-Ethoxy-4-(3-methyldodec-1-enyl)phenol

Starting from (4-(tert-butyldimethylsilyloxy)-3-ethoxyphenyl)methyltriphenyl-phosphonium bromide (2.14 g, 3.52 mmol, 1.0 equiv.), n-BuLi (1.6 M in hexanes, 2.2 mL, 3.52 mmol, 1.0 equiv.) and 2-methylundecanal (0.97 g, 5.28 mmol, 1.5 equiv.), a colorless oil was obtained after purification by flash chromatography on SiO$_2$ (hexanes/EtOAc 97:3) which was dissolved in THF. After treatment of that solution with n-Bu$_4$NF (1.0 M in THF, 3.0 mL, 2.97 mmol, 1.2 equiv.), 0.63 g (56% over 2 steps) of the title compound as a light yellow oil was obtained after purification by flash chromatography on SiO$_2$ (hexanes/EtOAc 98:2→9:1).

$^1$H-NMR (CDCl$_3$, 400 MHz): 6.88-6.77 (m, 3H), 6.28-6.22 (m, 1H), 5.91 (dd, J=15.8, 8.0 Hz, 0.7H), 5.61 (s, 0.3H), 5.61 (s, 0.7H), 5.33 (dd, J=11.6, 10.4 Hz, 0.3H), 4.16-4.08 (m, 2H), 2.77-2.69 (m, 0.3H), 2.28-2.19 (m, 0.7H), 1.47-1.43 (m, 3H), 1.36-1.23 (m, 16H), 1.06 (d, J=6.6 Hz, 2.1H), 1.03 (d, J=6.8 Hz, 0.9H), 0.90-0.86 (m, 3H).

MS (EI): 318 (M$^+$, 22), 303 (2), 191 (69), 164 (6), 145 (100), 117 (18), 91 (9), 77 (5), 55 (12), 43 (21).

14.2: 2-Ethoxy-4-((2-(2-(4-methylcyclohex-3-enyl)propyl)cyclopentylidene)methyl)-phenol)

Starting from (4-(tert-butyldimethylsilyloxy)-3-ethoxyphenyl)methyltriphenyl-phosphonium bromide (2.30 g, 3.79 mmol, 1.0 equiv.), n-BuLi (1.6 M in hexanes, 2.4 mL, 3.79 mmol, 1.0 equiv.) and 2-(2-(4-methylcyclohex-3-enyl)propyl)cyclo-pentanone (1.17 g, 5.30 mmol, 1.4 equiv.), a light yellow oil was obtained after purification by flash chromatography on SiO$_2$ (hexanes/EtOAc 99:1) which was dissolved in THF. After treatment of that solution with n-Bu$_4$NF (1.0 M in THF, 2.5 mL, 2.46 mmol, 1.2 equiv.), 0.19 g (14% over 2 steps) of the title compound as a viscous yellow oil was obtained after purification by flash chromatography on SiO$_2$ (hexanes/EtOAc 97:3→9:1).

$^1$H-NMR (CDCl$_3$, 400 MHz): 6.89-6.79 (m, 3H), 6.22-6.15 (m, 1H), 5.58 (s, 1H), 5.39-5.33 (m, 1H), 4.15-4.06 (m, 2H), 2.60-2.54 (m, 2H), 2.00-1.14 (m, 21H), 0.93-0.86 (m, 3H).

MS (EI): 354 (M$^+$, 100), 257 (25), 229 (10), 217 (35), 171 (45), 151 (24), 121 (18).

EXAMPLE 15

2-(5-(3-Isopropylphenyl)hex-2-en-2-yl)naphthalene

A solution of 1-(2-naphthyl)ethyltriphenylphosphonium bromide (2.30 g, 4.62 mmol, 1.0 equiv.) in THF (16 mL), was cooled to 0° C. After adding n-BuLi (1.6 M in hexanes, 2.9 mL, 4.62 mmol, 1.0 equiv.) at 0° C., the red-brown suspension was stirred at 0° C. for 15 min. 3-(3-Isopropylphenyl)butanal (1.32 g, 6.94 mmol, 1.5 equiv.) in THF (2 mL) was added, and the mixture was stirred at 0° C.→70° C. for 18 h. After addition of H$_2$O, the aqueous layer was extracted with hexanes (2x), the combined organic phases were washed with brine, dried (MgSO$_4$), filtered and the filtrate was concentrated. The residue was purified by flash chromatography on SiO$_2$ (cyclohexane/EtOAc 997:3) to yield 0.57 g (38%) of the title compound as a colorless viscous oil.

Odor description (dry-down of a 10% DPG solution after 24 hours on a smelling strip): floral, watery, powdery.

$^1$H-NMR (CDCl$_3$, 400 MHz): 7.84-7.73 (m, 4H), 7.54-7.40 (m, 3H), 7.28-7.18 (m, 1H), 7.13-6.93 (m, 3H), 5.94-5.90 (m, 0.75H), 5.54-5.50 (m, 0.25H), 2.97-2.73 (m, 2H), 2.57-2.52 (m, 1.5H), 2.36-2.23 (m, 0.5H), 2.09-2.07 (m, 3H), 1.38-1.20 (m, 9H).

MS (EI): 328 (M$^+$, 6), 181 (100), 165 (27), 147 (19), 115 (5), 105 (9), 91 (6), 77 (2), 43 (10).

EXAMPLE 16.1-16.5

Following the general procedure as described in Example 15 the following compounds have been prepared:

16.1: 2-((4E,8Z)-undeca-2.4.8-trien-2-yl)naphthalene

Starting from (1-(2-naphthyl)ethyltriphenylphosphonium bromide (2.40 g, 4.83 mmol, 1.0 equiv.), n-BuLi (1.6 M in hexanes, 3.0 mL, 4.83 mmol, 1.0 equiv.) and (2E,6Z)-Nona-2,6-dienal (1.00 g, 7.24 mmol, 1.5 equiv.), and after stirring the mixture at 25° C. for 3 h, 0.90 g (67%) of the title compound as a a colorless oil was obtained after purification by flash chromatography on SiO₂ (cyclohexane/EtOAc 997:3).

Odor description (dry-down of a 10% DPG solution after 24 hours on a smelling strip): floral, green, watery, fatty, dark tea, mimosa.

¹H-NMR (CDCl₃, 400 MHz): 7.85-7.78 (m, 4H), 7.70-7.64 (m, 1H), 7.50-7.39 (m, 2H), 6.63-6.51 (m, 1.6H), 6.22-6.15 (m, 0.4H), 5.93-5.86 (m, 0.8H), 5.76-5.69 (m, 0.2H), 5.50-5.26 (m, 2H), 2.31-2.20 (m, 6H), 2.13-1.96 (m, 3H), 1.00 (t, J=7.6 Hz, 2.3H), 0.93 (t, J=7.5 Hz, 0.7H).

MS (EI): 276 (M⁺, 25), 261 (1), 207 (100), 192 (57), 179 (45), 165 (40), 152 (13), 141 (11), 128 (8), 115 (9), 77 (9), 41 (18).

16.2: 2-((6E)-Dodeca-2.6-dien-2-yl)naphthalene

Starting from (1-(2-naphthyl)ethyltriphenylphosphonium bromide (4.50 g, 9.05 mmol, 1.0 equiv.), n-BuLi (1.6 M in hexanes, 5.7 mL, 9.05 mmol, 1.0 equiv.) and (E)-dec-4-enal (2.09 g, 13.6 mmol, 1.5 equiv.), and after stirring the mixture at 25° C. for 3 h, 1.16 g (44%) of the title compound as a light yellow oil was obtained after purification by flash chromatography on SiO₂ (cyclohexane).

Odor description (dry-down of a 10% DPG solution after 24 hours on a smelling strip): floral, orange, flowery, powdery, aldehydic, sharp green.

¹H-NMR (CDCl₃, 400 MHz): 7.85-7.77 (m, 4H), 7.64-7.58 (m, 1H), 7.50-7.41 (m, 2H), 5.99-5.95 (m, 0.6H), 5.58-5.31 (m, 2.4H), 2.37-1.95 (m, 9H), 1.42-1.21 (m, 6H), 0.91-0.87 (m, 3H).

MS (EI): 292 (M⁺, 5), 181 (100), 165 (28), 153 (5), 141 (5), 128 (2), 115 (2), 41 (5).

16.3: 2-(4-Methyltridec-2-en-2-yl)naphthalene

Starting from (1-(2-naphthyl)ethyltriphenylphosphonium bromide (6.40 g, 12.9 mmol, 1.0 equiv.), n-BuLi (1.6 M in hexanes, 8.0 mL, 12.9 mmol, 1.0 equiv.) and 2-methylundecanal (3.56 g, 19.3 mmol, 1.5 equiv.), and after stirring the mixture at 25° C. for 3 h, 0.94 g (23%) of the title compound as a colorless oil was obtained after purification by flash chromatography on SiO₂ (cyclohexane).

Odor description (dry-down of a 10% DPG solution after 24 hours on a smelling strip): floral, orange flower, soft, aldehydic.

¹H-NMR (CDCl₃, 400 MHz): 7.84-7.77 (m, 4H), 7.64-7.60 (m, 1H), 7.50-7.40 (m, 2H), 5.73 (dd, J=9.5, 1.4 Hz, 0.75H), 5.29 (dd, J=10.2, 1.4 Hz, 0.25H), 2.65-2.55 (m, 0.75H), 2.27-2.22 (m, 0.25H), 2.16 (d, J=1.3 Hz, 2.25H), 2.10 (d, J=1.5 Hz, 0.75H), 1.41-1.20 (m, 16H), 1.07 (d, J=6.6 Hz, 2.25H), 0.95 (d, J=6.6 Hz, 0.75H), 0.91-0.88 (m, 3H).

MS (EI): 322 (M⁺, 13), 307 (3), 195 (100), 179 (14), 165 (24), 155 (13), 141 (9), 128 (4), 115 (2), 43 (8).

16.4: 2-(5.7.7-Trimethyloct-2-en-2-yl)naphthalene

Starting from (1-(2-naphthyl)ethyltriphenylphosphonium bromide (2.80 g, 5.63 mmol, 1.0 equiv.), n-BuLi (1.6 M in hexanes, 3.5 mL, 5.63 mmol, 1.0 equiv.) and 3,5,5-trimethylhexanal (1.20 g, 8.44 mmol, 1.5 equiv.), and after stirring the mixture at 25° C. for 3 h, 0.73 g (46%) of the title compound as a colorless oil was obtained after purification by flash chromatography on SiO₂ (cyclohexane/EtOAc 997:3).

Odor description (dry-down of a 10% DPG solution after 24 hours on a smelling strip): floral, orange, flowery, slightly sweet, medicinal.

¹H-NMR (CDCl₃, 400 MHz): 7.84-7.78 (m, 4H), 7.63-7.60 (m, 1H), 7.48-7.41 (m, 2H), 6.01-5.96 (m, 0.75H), 5.60-5.55 (m, 0.25H), 2.30-1.86 (m, 5H), 1.78-1.55 (m, 1H), 1.40-1.35 (m, 1H), 1.18-1.13 (m, 1H), 1.03 (d, J=6.6 Hz, 2.25H), 0.95 (s, 6.7H), 0.89 (d, J=6.6 Hz, 0.75H), 0.85 (s, 2.3H).

MS (EI): 280 (M⁺, 13), 265 (1), 181 (100), 165 (26), 155 (8), 141 (3), 128 (3), 115 (3), 57 (14), 41 (8).

16.5: 2-[(11E)-trideca-2.11-dien-2-yl]naphthalene

Starting from (1-(2-naphthyl)ethyltriphenylphosphonium bromide (49.7 g, 100 mmol, 1.0 equiv.) in THF (400 mL), KʳBuO (110 mL, 110 mmol, 1.1 equiv., 1M in THF) and (E)-undec-9-enal (16.8 g, 120 mmol, 1.2 equiv.) in THF (100 mL), 16.6 g (53%) of the title compound was obtained after purification by flash chromatography on SiO₂ (hexane) as a light yellow oil.

Odor description (dry-down of a 10% DPG solution after 24 hours on a smelling strip): soft aldehydic metallic, floral.

¹H-NMR (CDCl₃, 400 MHz): 7.86-7.79 (m, 4H), 7.66-7.61 (m, 1H), 7.50-7.42 (m, 2H), 5.99 (ddd, J=1.0, 7.2, 7.2 Hz, 0.7H), 5.58 (ddd, J=1.2, 7.4, 7.4 Hz, 0.3H), 5.51-5.38 (m, 2H), 2.32-2.26 (m, 2H), 2.18-2.15 (m, 3H), 2.11-1.93 (m, 3H), 1.69-1.61 (m, 2H), 1.56-1.25 (m, 10H).

MS (EI): 306 (M⁺, 21), 291 (1), 181 (100), 168 (59), 155 (30), 141 (20), 128 (10), 115 (5), 55 (17), 41 (12).

EXAMPLE 17

4-(4-(3-Isopropylphenyl)pent-1-enyl)-1,2-dimethoxybenzene

A solution of (3,4-dimethoxyphenyl)methyltriphenylphosphonium bromide (4.93 g, 10.0 mmol, 1.0 equiv.) in THF (10 mL), was cooled to 0° C. After adding n-BuLi (1.6 M in hexanes, 6.3 mL, 10.0 mmol, 1.0 equiv.) at 0° C., the red suspension was stirred at 0° C. for 20 min. 3-(3-Isopropylphenyl)butanal (2.09 g, 11.0 mmol, 1.1 equiv.) in THF (11 mL) was added, and the mixture was stirred at 0° C.→25° C. for 16 h. After addition of H₂O at 25° C., the aqueous layer was extracted with hexanes (2×), the combined organic phases were dried (MgSO₄), filtered and the filtrate was concentrated. The residue was purified by flash chromatography on SiO₂ (hexanes/EtOAc 99:1→4:1) to yield 2.67 g (82%) of the title compound as a colorless oil.

¹H-NMR (CDCl₃, 400 MHz): 7.30-7.24 (m, 1H), 7.12-7.05 (m, 3H), 6.91-6.81 (m, 3H), 6.42-6.34 (m, 1H), 6.10-6.02 (m, 0.5H), 5.59 (td, J=11.6, 7.1 Hz, 0.5H), 3.91-3.89 (m, 6H), 2.97-2.86 (m, 2H), 2.68 (dt, J=7.2, 1.8 Hz, 1H), 2.60-2.53 (m, 0.5H), 2.48-2.41 (m, 0.5H), 1.36-1.27 (m, 9H).

MS (EI): 324 (M⁺, 6), 177 (100), 147 (9), 131 (7), 115 (5), 103 (5), 91 (8), 77 (3), 43 (7).

EXAMPLE 18.1

5-(4-(3-Isopropylphenyl)pent-1-enyl)benzo[d][1,3]dioxole

A solution of (benzo[d][1,3]dioxol-5-ylmethyl)triphenylphosphonium bromide (4.77 g, 10.0 mmol, 1.0 equiv.) in THF (20 mL), was cooled to 0° C. After adding n-BuLi (1.6 M in hexanes, 6.3 mL, 10.0 mmol, 1.0 equiv.) at 0° C., the dark red suspension was stirred at 0° C. for 10 min. 3-(3-Isopropylphenyl)butanal (1.90 g, 10.0 mmol, 1.0 equiv.) in THF (10 mL) was added, and the mixture was stirred at 0° C.→25° C. for 16 h. After addition of H₂O at 25° C., the aqueous layer was extracted with hexanes and MTBE, the combined organic phases were dried (MgSO$_4$), filtered and the filtrate was concentrated. The residue was purified by flash chromatography on SiO$_2$ (hexanes/EtOAc 4:1) to yield 2.35 g (75%) of the title compound as a yellow oil.

$^1$H-NMR (CDCl$_3$, 400 MHz): 7.29-7.24 (m, 1H), 7.11-7.04 (m, 3H), 6.88 (br. s, 0.6H), 6.81-6.72 (m, 2.4H), 6.36-6.30 (m, 1H), 6.04-5.98 (m, 0.6H), 5.97 (s, 0.8H), 5.94 (s, 1.2H), 5.55 (td, J=11.7, 7.0 Hz, 0.4H), 2.96-2.84 (m, 2H), 2.65-2.38 (m, 2H), 1.34-1.27 (m, 9H).

MS (EI): 308 (M$^+$, 13), 161 (88), 147 (28), 131 (100), 117 (6), 103 (45), 91 (11), 77 (16), 43 (16).

18.2: 5-(4-(4-Methoxyphenyl)-3-methylbut-1-enyl)benzo[d][1,3]dioxole

Potassium t-pentylat (1.7 M in toluene, 6.5 mL, 11.0 mmol, 1.1 equiv.) was added to a solution of (benzo[d][1,3]dioxol-5-ylmethyl)triphenylphosphonium bromide (4.77 g, 10.0 mmol, 1.0 equiv.) in THF (20 mL) at 25° C. After the dark red suspension was stirred at 25° C. for 15 min, 3-(4-methoxyphenyl)-2-methylpropanal (1.78 g, 10.0 mmol, 1.0 equiv.) in THF (10 mL) was added, and the mixture was stirred at 70° C. for 1.5 h. After addition of 20% aq. AcOH-solution (10 mL) at 25° C., the aqueous layer was extracted with MTBE, the combined organic phases were dried (MgSO$_4$), filtered and the filtrate was concentrated. The residue was purified by flash chromatography on SiO$_2$ (hexanes/EtOAc 19:1) to yield 2.20 g (74%) of the title compound as a yellow oil.

$^1$H-NMR (CDCl$_3$, 400 MHz): 7.13-7.05 (m, 2H), 6.91-6.60 (m, 5H), 6.30-6.23 (m, 1H), 6.03 (dd, J=15.8, 7.0 Hz, 0.8H), 5.95 (s, 0.4H), 5.94 (s, 1.6H), 5.43 (dd, J=11.6, 10.4 Hz, 0.2H), 3.81 (s, 2.3H), 3.80 (s, 0.7H), 3.05-2.97 (m, 0.2H), 2.78-2.53 (m, 2.8H), 1.09 (d, J=6.3 Hz, 2.3H), 1.05 (d, J=6.6 Hz, 0.7H).

MS (EI): 296 (M$^+$, 9), 175 (90), 145 (100), 121 (23), 115 (51), 91 (14), 77 (11).

18.3: 5-(4-(4-tert-Butylphenyl)-3-methylbut-1-enyl)benzo[d][1,3]dioxole

Potassium t-butylat (1 M in THF, 11 mL, 11.0 mmol, 1.1 equiv.) was added to a solution of (benzo[d][1,3]dioxol-5-ylmethyl)triphenylphosphonium bromide (4.77 g, 10.0 mmol, 1.0 equiv.) in THF (20 mL) at 25° C. After the dark red suspension was stirred at 25° C. for 10 min, 3-(4-tert-butylphenyl)-2-methylpropanal (2.04 g, 10.0 mmol, 1.0 equiv.) in THF (10 mL) was added, and the mixture was stirred at 70° C. for 1.5 h. After addition of 20% aq. AcOH-solution (10 mL) at 25° C., the aqueous layer was extracted with hexanes, the combined organic phases were dried (MgSO$_4$), filtered and the filtrate was concentrated. The residue was purified by flash chromatography on SiO$_2$ (hexanes/EtOAc 19:1) to yield 2.83 g (88%) of the title compound as a yellow oil.

$^1$H-NMR (CDCl$_3$, 400 MHz): 7.29-7.24 (m, 2H), 7.09-7.02 (m, 2H), 6.86-6.48 (m, 3H), 6.24-6.20 (m, 1H), 6.01 (dd, J=15.9, 7.1 Hz, 0.8H), 5.89 (s, 2H), 5.39 (dd, J=11.5, 10.4 Hz, 0.2H), 2.99-2.91 (m, 0.2H), 2.75-2.49 (m, 2.8H), 1.30-1.26 (m, 9H), 1.04 (d, J=6.4 Hz, 2.3H), 1.00 (d, J=6.6 Hz, 0.7H).

MS (EI): 322 (M$^+$, 5), 175 (100), 145 (97), 127 (6), 117 (34), 91 (13).

EXAMPLE 19

1-(tert-Butyl)-4-[4-(4-methoxyphenyl)-2-methylbut-3-en-1-yl]benzene

A solution of (4-methoxyphenyl)methyltriphenylphosphonium bromide (2.40 g, 5.18 mmol, 1.0 equiv.) in THF (10 mL), was cooled to 0° C. After adding n-BuLi (1.6 M in hexanes, 3.2 mL, 5.18 mmol, 1.0 equiv.) at 0° C., the red suspension was stirred at 0° C. for 15 min. 3-(4-tert-Butylphenyl)-2-methylpropanal (1.59 g, 7.77 mmol, 1.5 equiv.) in THF (4 mL) was added, and the mixture was stirred at 0° C.→25° C. for 12 h. After addition of H$_2$O at 25° C., the aqueous layer was extracted with hexanes, the combined organic phases were dried (MgSO$_4$), filtered and the filtrate was concentrated. The residue was purified by flash chromatography on SiO$_2$ (cyclohexane/EtOAc 995:5→99:1) to yield 1.33 g (83%) of the title compound as a colorless oil.

$^1$H NMR (CDCl$_3$, 400 MHz): 7.32-7.28 (m, 3H), 7.14-7.03 (m, 3H), 6.87-6.81 (m, 2H), 6.32-6.28 (m, 1H), 6.09 (dd, J=15.9, 7.1 Hz, 0.6H), 5.45 (dd, J=11.4, 10.4 Hz, 0.4H), 3.82 (s, 3H), 3.06-2.98 (m, 0.4H), 2.80-2.54 (m, 2.6H), 1.33 (s, 5.4H), 1.32 (s, 3.6H), 1.09 (d, J=6.6 Hz, 1.8H), 1.04 (d, J=6.6 Hz, 1.2H).

MS (EI): 308 (M$^+$, 2), 293 (1), 161 (100), 146 (5), 131 (5), 117 (8), 91 (8).

EXAMPLE 20

1-[(4Z)-hepta-1,4-dien-1-yl]-4-methoxybenzene

Following the general procedure as described in Example 19, starting from cis-3-hexenyltriphenylphosphonium iodide (6.50 g, 13.8 mmol, 1.0 equiv.), n-BuLi (9.5 mL, 15.1 mmol, 1.0 equiv., 1.6 M in hexane) and 4-methoxybenzaldehyde (2.25 g, 16.5 mmol, 1.2 equiv.), 2.60 g (93%) of the title compound (ratio (1E)-isomer: (1Z)-isomer=9:1) was obtained after purification by flash chromatography on SiO$_2$ (cyclohexane/EtOAc 99:1) as a colorless oil.

Odor description (dry-down of a 10% DPG solution after 24 hours on a smelling strip): green floral natural, mimosa linden blossom.

1H NMR (CDCl$_3$, 400 MHz): 7.31-7.23 (m, 2H), 6.90-6.83 (m, 2H), 6.41-6.32 (m, 1H), 6.07 (dd, J=15.9, 6.6 Hz, 0.9H), 5.59-5.40 (m, 2.1H), 3.81 (s, 3H), 3.08-2.87 (m, 2H), 2.15-2.03 (m, 2H), 1.01 (t, J=7.6 Hz, 2.7H), 0.98 (t, J=7.6 Hz, 0.3H).

MS (EI): 202 (M+, 33), 173 (56), 158 (33), 134 (100), 128 (17), 121 (40), 115 (29), 103 (11), 91 (26), 77 (17), 65 (10), 51 (8), 39 (10).

EXAMPLE 21

1-Isopropyl-3-[5-(4-methoxyphenyl)pent-4-en-2-yl]benzene

Potassium t-butylat (17.1 mL, 17.1 mmol, 1.0 equiv., 1M in THF) was added to a solution of (4-methoxyphenyl)methyltriphenylphosphonium bromide (7.90 g, 17.1 mmol, 1.0 equiv.) in THF (17 mL) at 25° C. After the dark red suspension was stirred at 25° C. for 10 min, 3-(3-isopropylphenyl)butanal (3.24 g, 17.1 mmol, 1.0 equiv.) in THF (8.5 mL) was added, and the mixture was stirred at 25° C. 12 h. After addition of 20% aq. AcOH-solution at 25° C., the aqueous layer was extracted with hexane. The combined organic phases were washed with MeOH/H$_2$O (4:1; 2-3x), dried (MgSO$_4$), filtered and the filtrate was concentrated. The residue was purified by flash chromatography on SiO$_2$ (cyclohexane/EtOAc 995:5→99:1) to yield 4.03 g (80%) of the title compound as a light yellow oil.

Odor description (dry-down of a 10% DPG solution after 24 hours on a smelling strip): green, floral, florhydral-like.

$^1$H-NMR (CDCl$_3$, 400 MHz): 7.27-7.18 (m, 3H), 7.09-7.03 (m, 3H), 6.89-6.82 (m, 2H), 6.38-6.32 (m, 1H), 6.02

(ddd, J=15.8, 8.0, 6.6 Hz, 0.55H), 5.54 (dt, J=11.6, 7.1 Hz, 0.45H), 3.83 (s, 1.4H), 3.81 (s, 1.6H), 2.94-2.81 (m, 2H), 2.64-2.37 (m, 2H), 1.32-1.25 (m, 9H).

MS (EI): 294 (M$^+$, 4), 147 (100), 131 (4), 115 (10), 105 (5), 91 (13), 77 (3), 43 (6).

EXAMPLE 22.1-22.2

Following the general procedure as described in Example 21 the following compounds have been prepared:

22.1:
1-Methoxy-4-[(5E)-undeca-1,5-dien-1-yl]benzene

Starting from (4-methoxyphenyl)methyltriphenylphosphonium bromide (14.0 g, 30.2 mmol, 1.0 equiv.), KtBuO (34 mL, 34.0 mmol, 1.1 equiv., 1M in THF) and (E)-dec-4-enal (5.59 g, 36.3 mmol, 1.2 equiv.), 5.59 g (72%) of the title compound was obtained after purification by flash chromatography on SiO2 (cyclohexane/EtOAc 99:1) as a light yellow oil.

Odor description (dry-down of a 10% DPG solution after 24 hours on a smelling strip): green, fatty, floral, (E)-dec-4-enal-like.

1H-NMR (CDCl$_3$, 400 MHz): 7.30-7.22 (m, 2H), 6.90-6.83 (m, 2H), 6.38-6.33 (m, 1H), 6.10 (dt, J=15.8, 6.7 Hz, 0.6H), 5.58 (dt, J=11.6, 7.1 Hz, 0.4H), 5.47-5.41 (m, 2H), 3.82 (s, 1.2H), 3.81 (s, 1.8H), 2.40 (dq, J=7.3, 1.8 Hz, 0.8H), 2.29-2.21 (m, 1.2H), 2.18-2.12 (m, 2H), 2.02-1.96 (m, 2H), 1.40-1.25 (m, 6H), 0.91-0.88 (m, 3H).

MS (EI): 258 (M$^+$, 4), 147 (100), 132 (4), 115 (10), 103 (5), 91 (13), 78 (3), 41 (5).

22.2:
1-Methoxy-4-(3-methyldodec-1-en-1-yl)benzene

Starting from (4-methoxyphenyl)methyltriphenylphosphonium bromide (6.00 g, 13.0 mmol, 1.0 equiv.), K$^t$BuO (14 mL, 14.2 mmol, 1.1 equiv., 1M in THF) and 2-methylundecanal (2.86 g, 15.5 mmol, 1.2 equiv.), 1.98 g (53%) of the title compound was obtained after purification by flash chromatography on SiO$_2$ (hexane/EtOAc 99:1) as a colorless oil.

Odor description (dry-down of a 10% DPG solution after 24 hours on a smelling strip): ciste, incense, aldehydic (2-methylundecanal-like).

$^1$H-NMR (CDCl$_3$, 400 MHz): 7.32-7.29 (m, 2H), 6.89-6.83 (m, 2H), 6.32-6.27 (m, 1H), 5.97 (dd, J=15.9, 7.8 Hz, 0.8H), 5.36 (dd, J=11.4, 10.4 Hz, 0.2H), 3.83 (s, 0.6H), 3.82 (s, 2.4H), 2.78-2.71 (m, 0.2H), 2.32-2.21 (m, 0.8H), 1.45-1.25 (m, 16H), 1.08 (d, J=6.6 Hz, 2.4H), 1.05 (d, J=6.8 Hz, 0.6H), 0.90 (t, J=6.8 Hz, 3H).

MS (EI): 288 (M$^+$, 9), 273 (1), 161 (100), 146 (5), 134 (6), 121 (14), 115 (4), 91 (6), 43 (5).

EXAMPLE 23

4-[3-Methyl-4-(m-tolyl)but-3-en-1-yl]phenol

Potassium f-butylat (45 mL, 45 mmol, 1.0 equiv., 1M in THF) and 4-[4-(tert-butyldimethylsilyloxy)phenyl]butan-2-one (12.5 g, 45 mmol, 1.0 equiv.) in THF (23 mL) were added simultaneously to a solution of (m-tolyl)methyltriphenylphosphonium bromide (20.1 g, 45 mmol, 1.0 equiv.) in THF (45 mL) at 70° C. The mixture was stirred at 70° C. for 16 h. After addition of 20% aq. AcOH-solution at 25° C., the aqueous layer was extracted with hexane. The combined organic phases were washed with MeOH/H$_2$O (4:1; 2-3×), dried (MgSO$_4$), filtered and the filtrate was concentrated. The residue was purified by flash chromatography on SiO$_2$ (cyclohexane/EtOAc 99:1) to yield tert-butyl{4-[4-(4-methoxyphenyl)-3-methylbut-3-en-1-yl]phenoxy}-dimethylsilane as a light yellow oil. This compound was dissolved in THF (32 mL), n-Bu$_4$NF (35 mL, 35 mmol, 0.8 equiv., 1.0 M in THF) was added, and the mixture was stirred at 25° C. for 1 h. After addition of H$_2$O, the aqueous layer was extracted with MTBE (2×), the combined organic phases were washed with brine, dried (MgSO$_4$), filtered and the filtrate was concentrated. The residue was purified by flash chromatography on SiO$_2$ (hexane/EtOAc 9:1→4:1) to yield 7.40 g (65% over 2 steps) of the title compound as a light yellow oil.

Odor description (dry-down of a 10% DPG solution after 24 hours on a smelling strip): raspberry, fruity, floral.

$^1$H-NMR (CDCl$_3$, 400 MHz): 7.24-7.18 (m, 1H), 7.12-6.94 (m, 5H), 6.80-6.74 (m, 2H), 6.31 (s, 0.4H), 6.24 (s, 0.6H), 4.67 (s, 0.6H), 4.66 (s, 0.4H), 2.80-2.74 (m, 2H), 2.52-2.48 (m, 0.8H), 2.46-2.42 (m, 1.2H), 2.36 (s, 1.8H), 2.34 (s, 1.2H), 1.94 (d, J=1.5 Hz, 1.2H), 1.91 (d, J=1.3 Hz, 1.8H).

MS (EI): 252 (M$^+$, 15), 145 (57), 129 (14), 115 (13), 107 (100), 91 (6), 77 (14).

EXAMPLE 24

Stability Tests

The stability of the compounds has been measured in standard consumer product bases (LD=liquid detergent base, FS=fabric conditioner, SH=shampoo). Therefore, the consumer product containing the compound of formula (I) were stored at room temperature for one day and then at 37° C. for up to three months. Samples have been taken after one day, one month and three months respectively. They have been diluted with acetone, and analyzed for the amount of unchanged compound (i.e. the amount of compound of formula (I)) left in the sample with HPLC, indicated as mol % recovery. The results are given in Table 1 below.

TABLE 1

Storage stability in liquid detergents, fabric softener and shampoo bases

| Compound | base | 1 day | 1 month | 3 months |
|---|---|---|---|---|
| Precursor Ex. 2.2 | LD | 100 | 94 | 93 |
|  | FS | 100 | 95 | 97 |
|  | SH | 100 | 97 | 94 |
| Precursor Ex. 3 | LD | 100 | 97 | 95 |
|  | SH | 98 | 100 |  |
| Precursor Ex. 2.6 | LD | 100 | 98 | 98 |
|  | SH | 100 | 97 | 97 |
| Precursor Ex. 12 | LD | 76 | 77 | 72 |
| Precursor Ex. 6.1 | LD | 88 | 89 | 87 |
|  | SH | 85 | 86 | 85 |
| Precursor Ex. 2.14 | LD | 99 | 98 | 93 |
|  | SH | 100 | 100 | 93 |
| Precursor Ex. 4.2 | LD | 100 | 96 | 98 |
|  | SH | 100 | 89 | 89 |
| Precursor Ex. 6.3 | LD | 100 | 100 | 97 |
|  | SH | 100 | 94 | 90 |
| Precursor Ex. 2.16 | LD | 100 | 95 | 92 |
|  | SH | 96 | 94 | 88 |
| Precursor Ex. 2.17 | LD | 100 | 96 | 96 |
|  | SH | 97 | 97 | 91 |
| Precursor Ex. 16.2 | LD | — | 100 | 100 |
|  | SH | — | 88 | 86 |
| Precursor Ex. 16.3 | LD | — | 99 | 100 |
|  | SH | — | 97 | 95 |

EXAMPLE 25

Application in Liquid Detergent

To a non fragranced heavy duty liquid detergent base (pH 8.4) was added 0.1% wt/wt of either, a compound of formula (I) or the corresponding free fragrant aldehyde/ketone and, when olfactively pure available, together with the corresponding carbonyl compound. A sample of this base (34 g) was used to wash a load of 5 cotton terry towels (ca. 200 g dry weight each, about 1 kg total load) in a standard frontloading European washing machine. The wash cycle was carried out at 40° C., followed by two cold rinse cycles and spinning at 1000 rpm. The washed towels were assessed blind by a panel of experienced evaluators for fragrance intensity at TO (wet if not otherwise stated) and after 24 h line dry at room temperature. The intensity was indicated according to the following scale: 0 (odorless), 1 (very weak), 2 (weak), 3 (medium), 4 (strong), 5 (very strong). The results are given in Table 2 below.

TABLE 2

Fragrance intensity of the free fragrant and a precursor releasing said fragrant

| Ingredient: Free fragrant Precursor | mean intensity at $T_0$ | mean intensity after 24 hours |
|---|---|---|
| Ethylvanillin | 1.3 | 0.6 |
| Precursor Ex. 3 | 3.4 | 2.3 |
| Nonadienal | 1.3 | 1.4 |
| Precursor Ex. 2.12 | 3.8 | 3.4 |
| Oranger Crist | 3.1 | 1.2 |
| Precursor Ex. 6.3 | 2.8 | 2.4 |
| trans-4-Decenal | 2.2 | 0.7 |
| Precursor Ex. 8.1 | 3.0 | 2.6 |
| Ethylvanillin + Raspberry Ketone | 2.6 | 1.1 |
| Precursor Ex. 12 | 3.2 | 2.0 |
| Benzaldehyde + Raspberry Ketone | 1.2 | 0.5 |
| Precursor Ex. 11 | 2.5 | 2.4 |
| Oranger Crist + 2-methylundecanal | 3.2 | 1.0 |
| Precursor Ex. 16.3 | 1.8 | 2.4 |
| Heliotropine + Lilial | 2.8 | 1.2 |
| Precursor Ex. 18.3 | 2.4 | 2.0 |

As can be seen from the results given in the Table 2 above, the compounds of formula (I) showed higher odor scores on dry clothes compared to the free aldehydes/ketones, thereby demonstrating a desired controlled release effect. For some of the dry clothes additional assessment was carried out after 5 days and the towels washed with the compounds of the present invention still showed perceivable odors whereas those washed with the free aldehydes/ketones were in general odorless.

EXAMPLE 26

Application in Fabric Conditioner

To a non fragranced fabric conditioner, containing 12% of the ester-quat type cationic surfactant Rewoquat WE18, was added 2% wt/wt of either, a compound of formula (I) or the corresponding free fragrant aldehyde/ketone as a 10% solution in dipropylene glycol (DPG).

A mixed load of fabric containing 4 cotton terry towels was rinsed with the fabric conditioner preparations described above (35 g). The washed towels were assessed wet ($T_0$) and after 24 hours line drying at room temperature for fragrance intensity by a panel experienced evaluators. The coded towels were assessed blind. The intensity was indicated according to the following scale: 0 (odorless), 2 (very weak), 4 (weak), 6 (medium), 8 (strong), 10 (very strong). The results are given in Table 3 below.

TABLE 3

Fragrance intensity of the free fragrant and a precursor releasing said fragrant

| Ingredient: Free fragrant Precursor | mean intensity at $T_0$ | mean intensity after 24 hours | mean intensity after 7 days |
|---|---|---|---|
| Ethylvanillin | 5.5 | 7.4 | — |
| Precursor Ex. 1 | 4.9 | 7.9 | — |
| 2,6-Nonadienal | 7.5 | 2.8 | 1.0 |
| Precursor Ex. 2.12 | 6.4 | 6.4 | 4.0 |
| Raspberry Ketone | 4.9 | 6.4 | — |
| Precursor Ex. 12 | 5.8 | 8.0 | — |
| Oranger Crist | 7.0 | 3.9 | 1.0 |
| Precursor Ex. 16.3 | 3.0 | 4.0 | 5.0 |
| Ethylvanillin | 7.2 | 7.5 | 4.0 |
| Precursor Ex. 4.2 | 5.5 | 6.8 | 6.0 |
| Florhydral | 6.4 | 4.2 | — |
| Precursor Ex. 2.6 | 3.0 | 5.3 | — |
| Oranger Crist | 7.0 | 3.9 | 1.0 |
| Precursor Ex. 16.2 | 3.6 | 7.0 | 3.5 |

The compounds of formula (I) showed higher odour scores on dry clothes compared to the free aldehydes/ketones, thereby demonstrating a desired controlled release effect. Furthermore, several towels were reassessed after 7 days and a further increase in fragrance intensity was noted for some of them.

EXAMPLE 27

Application in Powder Detergent

To a non fragranced bleach powder detergent base was added 0.1% wt/wt of either, a compound of formula (I) or the corresponding free fragrant aldehyde/ketone, as a 10% solution in DPG. The samples were stored at 37° C. for one month.

A mixed load of fabric (total 2.5 kg) containing 4 cotton terry towels for evaluation was washed in a standard front-loading washing machine using the above prepared powder detergent base (90 g). The wash cycle was carried out at 40° C., followed by two cold rinse cycles and spinning. The washed towels were assessed by a panel of 5 experienced evaluators for fragrance intensity after tumble drying and after 24 h line drying at room temperature. The intensity was indicated according to the following scale: 0 (odorless) to 10 (very strong). The coded towels were assessed blind. The results are given in Table 4 below.

TABLE 4

Fragrance intensity of the free fragrant and a precursor releasing said fragrant

| | mean intensity | | | |
|---|---|---|---|---|
| | Tumble dry | | line dry | |
| Ingredient: Free fragrant Precursor | 24 h | 7 d | 24 h | 7 d |
| Ethylvanillin | 3.0 | 1.3 | 1.5 | 1.3 |
| Precursor Ex. 3 | 7.0 | 4.3 | 6.0 | 4.0 |
| Ethylvanillin + Raspberry Ketone | 1.0 | 1.3 | 2.3 | 0.8 |
| Precursor Ex. 12 | 5.3 | 3.0 | 6.0 | 4.0 |

The compounds of the present invention showed higher odour scores on dry clothes after 24 hours and one week respectively compared to the free aldehyde/ketone, thereby demonstrating a desired controlled release effect. Almost all the performance of the raw materials was lost on storage, whereas the compounds of formula (I) largely maintained its level of performance.

The invention claimed is:
1. A method comprising providing a compound of formula (I)

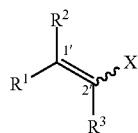
(I)

as precursor for generating in the presence of molecular oxygen a ketone or aldegyde of the formula (II)

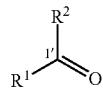
(II)

and a carbonyl compound of the formula (III)

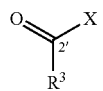
(III)

and exposing the precursor to oxygen;
wherein
$R^1$ is selected from the group consisting of
$C_5$-$C_{14}$ alkyl, $C_5$-$C_{14}$ alkenyl,
$C_5$-$C_6$ cycloalkyl, $C_5$-$C_8$ cycloalkyl substituted with 1, 2, or 3 groups selected from $C_1$-$C_6$ alkyl and $C_2$-$C_4$ alkylidene,
$C_5$-$C_8$ cycloalkenyl, $C_5$-$C_8$ cycloalkenyl wherein the cycloalkenyl-ring is substituted with 1, 2, or 3 groups selected from $C_1$-$C_4$ alkyl, $C_2$-$C_4$ alkylidene, and $C_3$-$C_5$ cycloalkyl,
$(C_1$-$C_3)$alkyl$(C_5$-$C_8)$cycloalkyl wherein the cycloalkyl-ring is optionally substituted with one group selected from —OH group and =O group, and/or one or two ether group(s), and/or up to four $C_1$-$C_5$ alkyl groups,
$(C_1$-$C_4)$alkyl$(C_5$-$C_6)$cycloalkenyl wherein the cycloalkenyl-ring is optionally substituted one —OH group, and/or one or two ether group(s) and/or up to four $C_1$-$C_5$ alkyl groups,
$(C_2$-$C_3)$alkenyl$(C_5$-$C_6)$cycloalkenyl wherein the cycloalkenyl-ring is optionally substituted with one —OH group, and/or one or two ether group(s), and/or up to four $C_1$-$C_5$ alkyl groups,
$C_6$-$C_{14}$ aryl,
$C_6$-$C_{14}$ aryl wherein the aryl-ring is substituted with up to 3 groups selected from $C_1$-$C_4$ alkyl, —O—$CH_2$—O—, and —$OR^{11}$ wherein $R^{11}$ is independently selected from hydrogen and $C_1$-$C_4$ alkyl,
$(C_1$-$C_3)$alkyl$(C_6$-$C_{14})$aryl,
$(C_1$-$C_3)$alkyl$(C_6$-$C_{14})$aryl wherein the aryl-ring is substituted with up to 2 groups selected from $C_1$-$C_4$ alkyl, —O—$CH_2$—O—, and —$OR^{12}$ wherein $R^{12}$ is independently selected from hydrogen and $C_1$-$C_4$ alkyl,
$(C_2$-$C_8)$alkenyl$(C_6$-$C_{14})$aryl,
$(C_2$-$C_8)$alkenyl$(C_6$-$C_{14})$aryl wherein the aryl-ring is substituted with up to 2 groups selected from $C_1$-$C_4$ alkyl, —O—$CH_2$—O—, and —$OR^{13}$ wherein $R^{13}$ is independently selected from hydrogen and $C_1$-$C_4$ alkyl, and
bi-, tri-, or tetracyclic hydrocarbon ring comprising $C_8$-$C_{12}$ carbon atoms optionally substituted with up to 6 groups selected from $C_1$-$C_4$ alkyl, —O—$CH_2$—O—, and —$OR^{14}$ wherein $R^{14}$ is independently selected from hydrogen and $C_1$-$C_4$ alkyl;
$R^2$ is selected from hydrogen, $C_1$-$C_5$ alkyl, and $C_2$-$C_5$ alkenyl;
or
$R^1$ and $R^2$ form together with the carbon atom to which they are attached
a) a 5 to 7 membered hydrocarbon ring(s), the ring(s) may optionally contain up to two ether groups, and/or the ring(s) may optionally be substituted with $C_1$-$C_5$ alkyl groups
b) 2-(2-(4-methylcyclohex-3-en-1-yl)propyl)cyclopent-1-ylidene, or
c) a 14-17 membered hydrocarbon ring, the ring may optionally be substituted with a methyl group;
$R^3$ is hydrogen or methyl; and
X means a radical of formula (Ia)

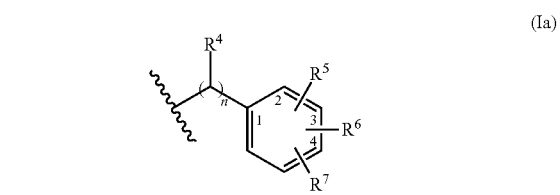
(Ia)

wherein n is 0 or 1;
$R^4$ is hydrogen or methyl;
$R^5$ is hydrogen or methyl;
$R^6$ is selected from hydrogen, $C_1$-$C_5$ alkyl, vinyl, hydroxys, methoxy or ethoxy; and
$R^7$ is selected from hydrogen, $C_1$-$C_5$ alkyl, vinyl, hydroxyl, methoxy or ethoxy;
with the proviso that if one of $R^6$ and $R^7$ is hydroxyl then the other of $R^6$ and $R^7$ is selected from methoxy or ethoxy;
or
$R^6$ and $R^7$ form together with the carbon atoms to which they are attached a 5 or 6 membered ring containing up to two oxygen atoms, wherein the ring may optionally be substituted with up to 6 methyl groups;
with the proviso that
a) if n=0, $R^1$ is not a group selected from aryl and aryl substituted with an —$OR^{11}$ wherein $R^{11}$ is hydrogen or $C_1$-$C_4$ alkyl; and
b) if $R^3$ is hydrogen and $R^1$ is selected from the group consisting of alkenyl, alkenylcycloalkenyl, alkenylaryl and cycloalkenyl in which no $sp^3$-hybirdised C-atom is between C-1' and the nearest C—C double bond of $R^1$, then n=1.

2. A method according to claim 1 of generating a carbonyl compound of the formula

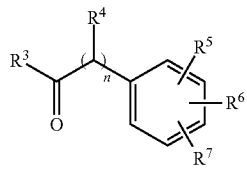

wherein n is 0 or 1;
R$^3$ is hydrogen or methyl;
R$^4$ is hydrogen or methyl;
R$^5$ is hydrogen or methyl;
R$^6$ is selected from hydrogen, C$_1$-C$_5$ alkyl, vinyl, hydroxyl, methoxy or ethoxy; and
R$^7$ is selected from hydrogen, C$_1$-C$_5$ alkyl, vinyl, hydroxyl, methoxy or ethoxy, with the proviso that if one of R$^8$ and R$^7$ is hydroxyl then the other of R$^6$ and R$^7$ is selected from methoxy or ethoxy;
or
R$^6$ and R$^7$ form together with the carbon atoms to which they are attached a 5 or 6 membered ring containing up to two oxygen atoms, wherein the ring may optionally be substituted with up to 6 methyl groups
characterized in that a compound of formula (I) is exposed to oxygen.

3. A method according to claim 2 wherein the carbonyl compound is selected from ethylvanilin, vanillin, 1-(naphthalen-2-yl)ethanone, acetophenone, 1,3-benzodioxole-5-carboxaldehyde, anisic aldehyde, veratric aldehyde, phenylacetic aldehyde, 4-methyl phenylacetaldehyde, benzaldehyde, 3-methyl-benzaldehyde, 1-(4-methoxyphenyl) ethanone, 4-(1-methylethyl)-benzenacetaldehyde, 2,4-(di-(1,1-dimethylethyl))-5-methoxy-benzaldehyde, 4-isopropyl-benzaldehyde, 1-(2,4-dimethyl phenyl)ethanone, 5,5,7,8,8-pentamethyl-5,6,7,8-tetrahydronaphthalene-2-carbaldehyde, 1-(3,5,5,6,8,8-hexamethyl-5,6,7,8-tetrahydronaphthalen-2-yl) ethanone, 1-(5,6,7,8-tetrahydronaphthalen-2-yl) ethenone, 1-(1,2,3,3,6-hexamethyl-2,3-dihydro-1H-inden-5-yl)ethanone, 2-(4-isopropyl phenyl)propanal, 3,5,5,6,7,8,8-heptamethyl-5,6,7,8-tetrahydronaphthalene-2-carbaldehyde, 2,3,3-trimethyl-2,3-dihydro-1H-inden-1-one, and mixtures thereof.

4. The method of claim 2 wherein the carbonyl compound is 4-methoxybenzaldehyde.

5. A method according to claim 1 of generating a fragrant aldehyde or ketone of the formula (II)

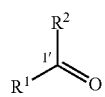

wherein
R$^1$ is selected from the group consisting of
C$_5$-C$_{14}$ alkyl, C$_5$-C$_{14}$ alkenyl,
C$_5$-C$_6$ cycloalkyl, C$_5$-C$_8$ cycloalkyl substituted with 1, 2, or 3 groups selected from
C$_1$-C$_6$ alkyl and C$_2$-C$_4$ alkylidene,
C$_5$-C$_8$ cycloalkenyl, C$_5$-C$_8$ cycloalkenyl wherein the cycloalkenyl-ring is substituted with 1, 2, or 3 groups selected from C$_1$-C$_4$ alkyl, C$_2$-C$_4$ alkylidene and C$_3$-C$_5$ cycloalkyl, (C$_1$-C$_3$)alkyl(C$_5$-C$_6$)cycloalkyl wherein the cycloalkyl-ring is optionally substituted with one group selected from —OH group and =O group, and/or one or two ether group(s), and/or up to four C$_1$-C$_5$ alkyl groups,
(C$_1$-C$_4$)alkyl(C$_5$-C$_6$)cycloalkenyl wherein the cycloalkenyl-ring is optionally substituted with one —OH group, and/or one or two ether group(s), and/or up to four C$_1$-C$_5$ alkyl groups,
(C$_2$-C$_3$)alkenyl(C$_5$-C$_6$)cycloalkenyl wherein the cycloalkenyl-ring is optionally substituted with one —OH group, and/or one or two ether group(s), and/or up to four C$_1$-C$_5$ alkyl groups,
C$_6$-C$_{14}$ aryl,
C$_6$-C$_{14}$ aryl wherein the aryl-ring is substituted with up to 3 groups selected from C$_1$-C$_4$ alkyl, —O—CH$_2$—O—, and —OR$^{11}$ wherein R$^{11}$ is independently selected from hydrogen and C$_1$-C$_4$ alkyl;
(C$_1$-C$_3$)alkyl(C$_6$-C$_{14}$)aryl,
(C$_1$-C$_3$)alkyl(C$_6$-C$_{14}$)aryl wherein the aryl-ring is substituted with up to 2 groups selected from C$_1$-C$_4$ alkyl, —O—CH$_2$—O—, and —OR$^{12}$ wherein R$^{12}$ is independently selected from hydrogen and C$_1$-C$_4$ alkyl,
(C$_2$-C$_8$)alkenyl(C$_8$-C$_{14}$)aryl,
(C$_2$-C$_8$)alkenyl(C$_8$-C$_{14}$)aryl wherein the aryl ring is substituted with up to 2 groups selected from C$_1$-C$_4$ alkyl, —O—CH$_2$—O—, and —OR$^{13}$ wherein R$^{13}$ is independently selected from hydrogen and C$_1$-C$_4$ alky, and
bi-, tri, or tetracyclic hydrocarbon ring comprising C$_8$-C$_{12}$ carbon atoms optionally substituted with up to 6 groups selected from C$_1$-C$_4$ alkyl, —O—CH$_2$—O—, and —OR$^{14}$ wherein R$^{14}$ is independently selected from hydrogen and C$_1$-C$_4$ alkyl;
R$^2$ is selected from hydrogen, C$_1$-C$_5$ alkyl, and C$_2$-C$_5$ alkenyl,
or
R$^1$ and R$^2$ form together with the carbon atom to which they are attached
a) a 5 to 7 membered hydrocarbon ring(s), the ring(s) may optionally contain up to two ether groups, and/or the ring(s) may optionally be substituted with C$_1$-C$_5$ alkyl groups
b) 2-(2-(4-methylcyclohex-3-en-1-yl)propyl)cyclopent-1-ylidene, or
c) a 14-17 membered hydrocarbon ring, the ring may optionally be substituted with a methyl group; and
R$^3$ is hydrogen or methyl;
characterized in that a compound of formula (I) is exposed to oxygen.

6. A method according to claim 5 wherein the generated fragrant aldehyde is selected from benzaldehyde, 2,6,10-trimethylundec-9-enal, 8,8-dimethyl-1,2,3,4,5,6,7,8-octahydro-naphthalene-2-carbaldehyde, (4-isopropyl-phenyl)-ethanal, 2,4-dimethyl-cyclohex-3-ene-1-carbaldehyde, 1,3,5-trimethyl-cyclohex-1-ene-4-carbaldehyde, 4-(4-hydroxy-4-methypentyl)-cyclohex-3-ene-1-carbaldehyde, hex-2-enal, hex-3-enal, 3-(3-tert-butylcyclohexyl)propanal, 2-(4-tert-pentylcyclohexyl)acetaldehyde, 3,5,5-trimethyl-hexanal, heptanal, 2,6-dimethyl-hept-5-enal, decanal, dec-9-enal, dec-4-en-1-al, 2-methyl-decanal, undec-10-en-1-al, undecanal, dodecanal, 2-methyl-undecanal, tridecanal, tridec-2-enal, octanal, nonanal, non-2-enal, undec-9-enal, 2-phenyl-propanal, 2-(4-methyl-phenyl)-ethanal, 2-(4-methoxyphenyl)acetaldehyde, 3,7-dimethyl-octanal, 3,7,11-trimethyldodeca-6,10-dienal, 7-hydroxy-3,7-dimethyl-octanal, 2,6-dimethyl-oct-5-en-1-al, 3-(3-isopropyl-phenyl)butanal, 4-(4-methyl-pent-3-enyl)-cyclohex-3-ene-t-carbaldehyde, 2,3,5,5-tetramethyl-hexanal, decahydro-4,8,8-trimethyl-1,4- methanoazulene-9-carboxaldehyde, 2-methyl-3-(4-tert-butyl phenyl)-propanal, 3-(4-tert-butyl-phenyl)-propanal, 3-(4-isobutyl-phenyl)-propanal, 3-(benzo-[1,3]dioxol-5-yl)-2-methyl-propanal, 3,7-dimethyl-oct-6-ene-1-al, 3,7-dimethyl-octanal, 2-methyl-3-(4-isopropylphenyl)-propanal, 4-tert-butyl-cyclohexane-1-carbaldehyde, 4-(octahydro-4,7-methano-5 H-inden-5-ylidene)-butanal, (3,7-dimethyl-oct-6-enyloxy)-ethanal, 2(E),6(Z)-nonadienal 2,4-dimethyl-2,6-heptadienal, (E)-dec-2-enal, dodec-2-enal, 3,7-dimethyl-octa-2,6-dienal, 2,4-diethyl-hepta-2,6-dienal, 3,7-dimethyl-nona-2,6-dienal, 2-propyl-hept-2-enal, 3-(4-methoxyphenyl)-2-methylpropanal, 4-methoxybenzaldehyde, 1,3-benzodioxole-5-carboxaldehyde, 2,6,6-trimethylcyclohexa-1,3-dienecarbaldehyde, 4-((6-methylhepta-2-yl)oxy)butenal, 3-(4-ethylphenyl)-2,2-dimethylpropanal, (E)-2-benzylideneheptanal, cinnamaldehyde, 3-(3,3-dimethyl-2,3-dihydro-1H-inden-5-yl)propanal, 2-methyl-4-(2,6,6-trimethylcyclohex-2-en-1-yl)butanal, 4-isopropenyl-cyclohex-1-ene-1-carbaldehyde, and mixtures thereof.

7. A method according to claim 5 wherein the generated fragrant ketone is selected from 4-(4-hydroxyphenyl)butan-2-one, alpha-Ionone, dihydro alpha-Ionole, dihydro beta-Ionone, 1-(2,6,6-trimethyl-2-cyclohexen-1-yl)-1,6-hepta-dien-3-one, beta-Ionone, 1-(2,6,6-trimethylcyclohex-2-en-1-yl)pent-1-en-3-one, 2-methyl-1-(2,6,6-trimethylcyclohex-2-en-1-yl)pent-1-en-3-one, 3-methyl-4-(2,6,6-trimethylcyclohex-2-en-1-yl)but-3-en-2-one, 2-(2-(4-methylcyclohex-3-en-1-yl)propyl)cyclopentanone, 3-(2-oxopropyl)-2-pentylcyclopentanone, acetophenone, 1-(naphthalen-2-yl)ethanone, 4-(benzo[d][1,3]dioxol-5-yl) butan-2-one, and mixtures thereof.

8. The method of claim 1 wherein the compound of formula (I) is selected from the group consisting of (3-methyl-5-(2,6,6-trimethylcyclohex-1-enyl)pent-2-enyl)benzene; (5,9-dimethyldec-2-enyl)benzene; (4methyltridec-2-enyl)benzene; (3-(2,4-dimethylcyclohex-3-enyl)allyl)benzene; (4-methyldodec-2-enyl)benzene; 1-isopropyl-3-(6-phenylhex-4-en-2-yl)benzene; but-2-ene-1,3-diyldibenzene; ((4E)-3-methyl-5-(2,6,6-trimethylcyclohex-1-enyl)penta-2,4-dieny 1)benzene ; (3-methyldodec-2-enyl 1)benzene; 5-(3-methyl-5-phenyl-pent-3-enyl)benzo[d][1,3]dioxole; ((4E)-3,4-dimethyl-5-(2,6,6-trimethylcyclohex-2-enyl)penta-2,4-dienyl)benzene; (4E,8Z)-undeca-2,4,8-trienylbenzene; (6E)-dodeca-b 2,6-dienylbenzene; 1-tert-butyl-4-(2-methyl-5-phenylpent-3-enyl) benzene; 1-(2,2-dimethyl-5-phenylpent-3-enyl)-4-ethylbenzene; (5,7,7-trimethyloct-2-enyl)benzene; (6-(6-methylheptan-2-yloxy)hex-2-enyl)benzene; (5-(3-tert-utylcyclohexyl)pent-2-enyl)benzene; (4-(4-tert-pentylcyclohexyl)but-2-enyl)benzene; 2-ethoxy-4-(3-phenylprop-1-enyl)phenol; 4-(3-methyl-5-phenylpent-3-enyl)phenol; 2-ethoxy-4-(3-p-tolylprop-1-enyl)phenol; 2-ethoxy-4-(3-(4-methoxyphenyl)prop-1-enyl)phenol; 1-methoxy-4-(4-methyltridec-2-enyl)benzene; 1-isopropyl-3-(6-(4-methoxyphenyl)hex-4-en-2-yl)benzene; 1-((6E)-dodeca-2,6-dienyl)-4-methoxybenzene; 2-(4-(4-methoxyphenyl)but-2-en-2-yl)naphthalene; 1-tert-butyl-4-(5-(4-methoxyphenyl)-2-methylpent-3-enyl)benzene; 1-methyl-4-(4-methyltridec-2-enyl)benzene; 1-((6E)-dodeca-2,6-dienyl)-4-methylbenzene; 1-tert-butyl-4-(2-methyl-5-p-tolylpent-3enyl)benzene; 1-methyl-4-((4E)-3-methyl-5-(2,6,6-trimethylcyclohex-1-en-yl)penta-2,4-dien-1-yl) benzene; 5-(3-p-tolylprop-1-enyl)benzo[d][1,3]dioxole; 2-(4-methyltridec-2-enyl)naphthalene; 4-(3-methyl-4-phenylbut-3-enyl)phenol; 2-ethoxy-4-(4-hydroxyphenyl)-2-methylbut-1-enyl)phenol; 2-ethoxy-4-(4-(3-isopropylphenyl)pent-1-enyl)phenol; 2-ethoxy-4-(3-methyldodec-1-enyl) phenol; 2-ethoxy-4-((2-(2-(4-methylcyclohex-3-enyl) propyl)cyclopentylidene)methyl)-phenol; 2-(5-(3-isopropylphenyl)hex-2-en-2-yl)naphthalene; 2((4E,8Z)-undeca-2,4,8-trien-2-yl)naphthalene; 2-((6E)-dodeca-2,6-dien-2-yl)naphthalene; 2-(4-methyltridec-2-en-2-yl) naphthalene; 2-(5,7,7-trimethyloct-2-en-2-yl)naphthalene; 4-(4-(3-isopropylphenyl)pent-1-enyl)-1,2-dimethoxybenzene; 1,2-dimethoxy-4-(4-(4-methoxyphenyl)-3-methylbut-1-enyl)benzene; 5-(4-(3-isopropylphenyl)pent-1-enyl)benzo [d][1,3]dioxole; 5-(4-(4-methoxyphenyl)-3-methylbut-1-enyl)benzo [d][1,3]dioxole; 5-(4-(4-tert-butylphenyl)-3-methylbut-1-enyl)benzo[d][1,3]dioxole; 1-methoxy-4-(3-(p-tolyl)prop-1-en-1-yl)benzene; 1-(tert-butyl)-4-(4-(4-methoxyphenyl)-2-methylbut-3-en-1-yl)benzene; 4-(4-(4-methoxyphenyl)-3-methylbut-3-en-1-yl)phenol; 1-isopropyl-3-(5-(4-methoxyphenyl)pent-4-en-2-yl)benzene; 1-isobutyl-4-4-(4-methoxyphenyl)but-3-en-1-yl)benzene; 2-((11E)-tridec-2,11-dien-2-yl)naphthalene; 5-(4-phenylbut-1-en-1-yl)benzo [d][1,3]dioxole; 1,2-dimethoxy-4-(3-(4-(prop-1-en-2-yl)cyclohex-1-en-1-yl)allyl)benzene; 2-(5-(4-(tert-butyl)phenyl)-4-methylpent-2-en-2-yl)naphthalene; 2-((4E)-5,9-dimethyldeca-2,4,8-trien-2-yl)naphthalene; 2-(5-phenylpent-2-en-2-yl)naphthalene; 2-((4E)-tetradeca-2,4-dien-2-yl)naphthalene; 3-(3-(4-methoxyphenyl)-2-methylallyl)-2-pentylcyclopentanone; 1-methoxy-4-[(5E)-undeca-1,5-dien-1-yl]benzene; 1-methoxy-4-(3-methyldodec-1-en-1-yl)benzene; (1 E)-1-[(4Z)-hepta-1,4-dien-1-yl]-4-methoxybenzene; (1Z)-1-[(4Z)-hepta-1,4-dien-1-yl]-4-methoxybenzene; and 4-[3-methyl-4-(m-tolyl)but-3-en-1-yl]phenol.

9. A compound elected from the group consisting of (3-methyl-5-(2,6,6-trimethylcyclohex-1-enyl)pent-2-enyl)benzene; (5,9-dimethyldec-2-enyl)benzene; (4-methyltridec-2-enyl)benzene; (3-(2,4-dimethylcyclohex-3-enyl)allyl)benzene; (4-methyldodec-2-enyl) benzene; 1-isopropyl-3-(6-phenylhex-4-en-2-yl)benzene; but-2-ene-1,3-diyldibenzene; ((4E)-3-methyl-5-(2,6,6-trimethylcyclohex-1-enyl)penta-2,4-dienyl) benzene; (3-methyldodec-2-enyl)benzene; 5-(3-methyl-5-phenylpent-3-enyl)benzo[d][1,3]dioxole; ((4E)-3,4-dimethyl-5-(2,6,6-trimethylcyclohex-2-enyl) penta-2,4-dienyl)benzene; (4E,8Z)-undeca-2,4,8-trienylbenzene; (6E)-dodeca-2,6-dienylbenzene; 1-tert-butyl-4-(2-methyl-5-phenylpent-3-enyl)benzene; 1-(2,2-dimethyl-5-phenylpent-3-enyl)-4-ethylbenzene; (5,7,7-trimethyloct-2-enyl)benzene; (6-(6-methylheptan-2-yloxy)hex-2-enyl)benzene; (5-(3-tert-utylcyclohexyl) pent-2-enyl)benzene; (4-(4-tert-pentylcyclohexyl)but-2-enyl)benzene; 2-ethoxy-4-(3-phenylprop-1-enyl) phenol; 4-(3-methyl-5-phenylpent-3-enyl)phenol; 2-ethoxy-4-(3-p-totylprop-1-enyl)phenol; 2-ethoxy-4-(3-(4-methoxyphenyl)prop-1-enyl)phenol; 1-methoxy-4-(4-methyltridec-2-enyl)benzene; 1-isopropyl-3-6-(4-methoxyphenyl)hex-4-en-2-yl)benzene; 1-((6E)-dodeca-2,6-dienyl)-4-methoxybenzene; 2-(4-(4-methoxyphenyl)but-2-en-2-yl)naphthalene; 1-tert-butyl-4-(5(4-methoxyphenyl)-2-methylpent-3-enyl) benzene; 1-methyl-4-(4-methyltridec-2-enyl)benzene; 1-((6E)-dodeca-2,6-dienyl)-4-methylbenzene; 1-tert-butyl-4-(2-methyl-5-p-tolylpent-3-enyl)benzene; 1-methyl-4-((4E)-3-methyl-5-(2,6,6-trimethylcyclohex-1-en-yl)penta-2,4-dien-1-yl)benzene; 5-(3-p-tolylprop-1-enyl)benzo[d][1,3]-dioxole; 2-(4-methyltridec-2-enyl) naphthalene; 4-(3-methyl-4-phenylbut-3-enyl)phenol; 2-ethoxy-4-(4-(4-hydroxyphenyl)-2-methylbut-1-enyl) phenol; 2-ethoxy-4-(4-(3-isopropylphenyl)pent-1-enyl) phenol; 2-ethoxy-4-(3-methyldodec-1-enyl)phenol;

2-ethoxy-4-((2-(2-(4-methylcyclohex-3-enyl)propyl) cyclopentylidene)methyl)phenol; 2-(5-(3-isopropylphenyl)hex-2-en-2-yl)naphthalene; 2-((4E,8Z)-undeca-2,4,8-trien-2-yl)naphthalene; 2-((6E)-dodeca-2,6-dien-2-yl)naphthalene; 2-(4-methyltridec-2-en-2-yl) naphthalene: 2-(5,7,7-trimethyloct-2-en-2-yl) naphthalene; 4-(4-(3-isopropylphenyl)pent-1-enyl)-1, 2-dimethoxybenzene; 1,2-dimethoxy-4-(4-(4-methoxyphenyl)-3-methylbut-1-enyl)benzene; 5-(4-(3-isopropylphenyl)pent-1-enyl)benzo[d][1,3]dioxole; 5-(4-(4-methoxyphenyl)-3-methylbut-1-enyl)benzo[d] [1,3]-dioxole; 5-(4-(4-tert-butylphenyl)-3-methylbut-enyl)benzo[d][1,3]dioxole; 1-methoxy-4-(3-(p-tolyl) prop-1-en-1-yl)benzene; 1-(tert-butyl)-4-(4-(4-methoxyphenyl)-2-methylbut-3-en-1-yl)benzene; 4-(4-(4-methoxyphenyl)-3-methylbut-3-en-1-yl)phenol; 1-isopropyl-3-(5-(4-methoxyphenyl)pent-4-en-2-yl) benzene; 1-isobutyl-4-(4-(4-methoxyphenyl)but-3-en-1-yl)benzene; 2-((11E)-trideca-2,11-dien-2-yl)naphthalene; 5-(4-phenylbut-1-en-1-yl)benzo[d][1,3] dioxole; 1,2-dimethoxy-4-(3-(4-(prop-1-en-2-yl) cyclohex-1-en-1-yl)allyl)benzene; 2-(5-(4-(tert-butyl) phenyl)-4 -methylpent-2-en-2-yl)naphthalene; 2-((4E)-5,9-dimethyldeca-2,4,8-trien-2-yl)naphthalene; 2-(5-phenylpent-2-en-2-yl)naphthalene; 2-((4E)-tetradeca-2,4-dien-2-yl)naphthalene; 3-(3-(4-methoxyphenyl)-2-methylallyl)-2-pentylcyclopentanone; 1-methoxy-4-[(5E)-undeca-1,5-dien-1-yl]benzene; 1-methoxy-4-(3-methyldodec-1-en-1-yl)benzene; (1E)-1-[(4Z)-hepta-1, 4-dien-1-yl]-4-methoxybenzene; (1Z)-1-[(4Z)-hepta-1, 4-dien-1-yl]-4-methoxybenzene; and 4-[3-methyl-4-(m-tolyl)but-3-en-1-yl]phenol.

10. A consumer product comprising a compound of formula (I)

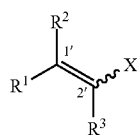

(I)

wherein the compound of formula (I) is capable of generating in the presence of molecular oxygen a ketone or aldehyde of formula(II)

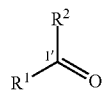

(II)

and a carbonyl compound of formula (III)

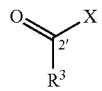

(III)

wherein
$R^1$ is selected from the group consisting of
$C_5$-$C_{14}$ alkyl, $C_5$-$C_{14}$ alkenyl, $C_5$-$C_6$ cycloalklyl, $C_5$-$C_8$ cycloalkyl substituted with 1, 2, of 3 groups selected from $C_1$-$C_6$ alkyl and $C_2$-$C_4$ alkylidene, $C_5$-$C_8$ cycloalkenyl, $C_5$-$C_8$ cycloakenyl wherein the cycloalkenyl-ring is substituted with 1, 2, or 3 groups selected from $C_1$-$C_4$ alkyl, $C_2$-$C_4$ alkylidene, and $C_3$-$C_5$ cycloalkyl, ($C_1$-$C_3$)alkyl($C_5$-$C_6$)cycloalkyl wherein the cycloalkyl-ring is optionally substituted with one group selected from —OH group and =O group, and/or one or two ether group(s), and/or up to four $C_1$-$C_5$ alkyl groups, ($C_1$-$C_4$)alkyl($C_5$-$C_6$)cycloalkenyl wherein the cycloalkenyl-ring is optionally substituted one —OH group, and/ or one or two ether group(s), and/or up to four $C_1$-$C_5$ alkyl groups, ($C_2$-$C_3$)alkenyl($C_5$-$C_6$)cycloalkenyl wherein the cycloalkenyl-ring is optionally substituted with one —OH group, and/or one or two ether group(s), and/or up to four $C_1$-$C_5$ alkyl groups, $C_6$-$C_{14}$ aryl, $C_6$-$C_{14}$ aryl wherein the aryl-ring is substituted with up to 3 groups selected from $C_1$-$C_4$ alkyl, —O—$CH_2$—O—, and —$OR^{11}$ wherein $R^{11}$ is independently selected from hydrogen and $C_1$-$C_4$ alkyl, ($C_1$-$C_3$)alkyl($C_6$-$C_{14}$)aryl, ($C_1$-$C_3$)alkyl($C_6$-$C_{14}$)aryl wherein the aryl-ring is substituted with up to 2 groups selected from $C_1$-$C_4$ alkyl, —O—$CH_2$—O—, and —$OR^{12}$ wherein $R^{12}$ is independently selected from hydrogen and $C_1$-$C_4$ alkyl, ($C_2$-$C_8$)alkenyl($C_6$-$C_{14}$)aryl, ($C_2$-$C_8$)alkenyl($C_6$-$C_{14}$)aryl wherein the aryl-ring is substituted with up to 2 groups selected from $C_1$-$C_4$ alkyl, —O—$CH_2$—O—, and —$OR^{13}$ wherein $R^{13}$ is independently selected from hydrogen and $C_1$-$C_4$ alkyl, and bi-, tri, or tetracyclic hydrocarbon ring comprising $C_8$-$C_{12}$ carbon atoms optionally substituted with up to 6 groups selected from $C_1$-$C_4$ alkyl, —O—$CH_2$—O—, and —$OR^{14}$ wherein $R^{14}$ is independently selected from hydrogen and $C_1$-$C_4$ alkyl;

$R^2$ is selected from hydrogen, $C_1$-$C_5$ alkyl, and $C_2$-$C_5$ alkenyl;

or $R^1$ and $R^2$ form together with the carbon atom to which they are attached a) a 5 to 7 membered hydrocarbon ring(s), the ring(s) may optionally contain up to two ether groups, and/or the ring(s) may optionally be substituted with $C_1$-$C_5$ alkyl groups b) 2-(2-4-methylcyclohex-3-en-1-yl)propyl)cyclopent-1-ylidene, or c) a 14-17 membered hydrocarbon ring, the ring may optionally be substituted with a methyl group;

$R^3$ is hydrogen or methyl; and

X means a radical of formula (Ia)

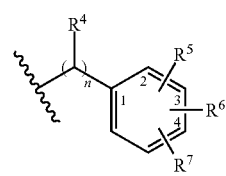

(Ia)

wherein n is 0 or 1;
$R^4$ is hydrogen or methyl;
$R^5$ is hydrogen or methyl;

$R^6$ is selected from hydrogen, $C_1$-$C_5$ alkyl, vinyl, hydroxy, methoxy or ethoxy; and $R^7$ is selected from hydrogen, $C_1$-$C_5$ alkyl vinyl, hydroxyl, methoxy or ethoxy;

with the proviso that if one of $R^6$ and $R^7$ is hydroxyl then the other of $R^6$ and $R^7$ is selected from methoxy or ethoxy;

or $R^6$ and $R^7$ form together with the carbon atoms to which they are attached a 5 or 6 membered ring containing up to two oxygen atoms, wherein the ring may optionally be substituted with up to 6 methyl groups;

with the proviso that a) if n=0, $R^1$ is not a group selected from aryl and aryl substituted with an —$OR^{11}$ wherein $R^{11}$ is hydrogen or $C_1$-$C_4$ alkyl; and b) if $R^3$ is hydrogen and $R^1$ is selected from the group consisting of alkenyl, alkenylcycloalkenyl, alkenylaryl and cycloalkenyl in which no $sp^3$-hybridised C-atom is between C-1' and the nearest C—C double bond of $R^1$, then n=1;

and a product base selected from the group consisting of home care products, personal care products and cleaning products.

* * * * *

UNITED STATES PATENT AND TRADEMARK OFFICE
CERTIFICATE OF CORRECTION

PATENT NO. : 9,193,935 B2
APPLICATION NO. : 13/996158
DATED : November 24, 2015
INVENTOR(S) : Baumgartner et al.

It is certified that error appears in the above-identified patent and that said Letters Patent is hereby corrected as shown below:

In the claims,

In claim 1, column 33, line 20; the term "aldegyde" is a misspelling. Claim 1 should read "...a ketone or aldehyde...".

In claim 1, column 33, line 48; the description of $R^1$ in formulas (I) and (II) is incorrect. Claim 1 should read "...$(C_1-C_3)$alkyl$(C_5-C_6)$cycloalkyl...".

In claim 1, column 34, line 45; the term "hydroxys" is a misspelling. Claim 1 should read "...vinyl, hydroxyl, methoxy...".

In claim 1, column 34, line 65; the term "hybirdised" is a misspelling. Claim 1 should read "...$sp^3$-hybridised C-atom...".

In claim 2, column 35, line 19; the recitation of $R^8$ is incorrect. Claim 2 should read "...if one of $R^6$ and $R^7$ is hydroxyl...".

In claim 3, column 35, lines 42-43; the term "1-(1,2,3,3,6-hexamethyl-2,3-dihydro-I H-inden-5-yl)ethanone" is a misspelling. Claim 3 should read "1-(1,1,2,3,3,6-hexamethyl-2,3-dihydro-I H-inden-5-yl)ethanone".

In claim 5, column 36, line 23; the description of $R^1$ in formula (II) is incorrect. Claim 5 should read "....$(C_2-C_8)$alkenyl$(C_6-C_{14})$aryl...".

In claim 5, column 36, line 24; the description of $R^1$ in formula (II) is incorrect. Claim 5 should read "....$(C_2-C_8)$alkenyl$(C_6-C_{14})$aryl...".

In claim 6, column 37, line 15; the term "4-((6-methylheptan-2-yl)oxy)butenal" is a misspelling. Claim 6 should read "4-((6-methylheptan-2-yl)oxy)butanal".

Signed and Sealed this
Second Day of August, 2016

Michelle K. Lee
*Director of the United States Patent and Trademark Office*

CERTIFICATE OF CORRECTION (continued)
U.S. Pat. No. 9,193,935 B2

In claim 7, column 37, line 23; the term "dihydro alpha-lonole" is a misspelling. Claim 7 should read "dihydro alpha-lonone".

In claim 8, column 37, line 44; the term "(6$E$)-dodeca-b 2,6-dienylbenzene" is a misspelling. Claim 8 should read "(6$E$)-dodeca-2,6-dienylbenzene".

In claim 9, column 38, line 31; the term "elected" is a misspelling. Claim 9 should read "selected".

In claim 9, column 38, line 51; the term "2-ethoxy-4-(3-p-totylprop-1-enyl)phenol" is a misspelling. Claim 9 should read "2-ethoxy-4-(3-p-tolylprop-1-enyl)phenol".

In claim 10, column 41, line 2; the term "hydroxy" is a misspelling. Claim 10 should read "hydroxyl".